(12) United States Patent
Srinivasan et al.

(10) Patent No.: US 10,398,691 B2
(45) Date of Patent: Sep. 3, 2019

(54) METHODS OF TREATING DEPRESSION

(71) Applicant: Rundle Research, LLC, Corona Del Mar, CA (US)

(72) Inventors: Sundar Srinivasan, Corona Del Mar, CA (US); Christina Chow, Seattle, WA (US)

(73) Assignee: RUNDLE RESEARCH, LLC, Corona del Mar, CA (US)

( * ) Notice: Subject to any disclaimer, the term of this patent is extended or adjusted under 35 U.S.C. 154(b) by 27 days.

(21) Appl. No.: 15/838,944

(22) Filed: Dec. 12, 2017

(65) Prior Publication Data

US 2018/0280382 A1 Oct. 4, 2018

Related U.S. Application Data

(63) Continuation-in-part of application No. 15/474,675, filed on Mar. 30, 2017, now abandoned.

(51) Int. Cl.
*A61K 31/495* (2006.01)
*A61P 25/24* (2006.01)
*A61K 45/06* (2006.01)

(52) U.S. Cl.
CPC ............ *A61K 31/495* (2013.01); *A61K 45/06* (2013.01); *A61P 25/24* (2018.01)

(58) Field of Classification Search
None
See application file for complete search history.

(56) References Cited

U.S. PATENT DOCUMENTS 5,648,396 A 7/1997 Young et al.
2015/0297585 A1 10/2015 Morillo

FOREIGN PATENT DOCUMENTS

WO WO 2015/136446 A1 9/2015

OTHER PUBLICATIONS

Areberg, Johan, et al. "Population Pharmacokinetic Meta-Analysis of Vortioxetine in Healthy Individuals." Basic & Clinical Pharmacology & Toxicology (2014); 115.6: 552-559.
Areberg, Johan, et al. "The Clinical Pharmacokinetics of Lu AA21004 and its Major Metabolite in Healthy Young Volunteers." Basic & Clinical Pharmacology & Toxicology (2012); 111: 198-205.
Brintellix (vortioxetine), "Highlights of Prescribing Information", Reference ID: 3381579, Sep. 2013; Takeda Pharmaceuticals America, Inc. [retrieved Jun. 5, 2017]. Retrieved from the Internet: https://www.accessdata.fda.gov/drugsatfda_docs/label/2013/204447s000lbl.pdf, 29 pages.
Forte, Roberta, et al. "The body fat-cognition relationship in healthy older individuals: Does gynoid vs android distribution matter?." The Journal of Nutrition, Health & Aging (2016); 21.3: 284-291.
Gluck, Marci E., et al. "Night Eating Syndrome Is Associated with Depression, Low Self-Esteem, Reduced Daytime Hunger, and Less Weight Loss in Obese Outpatients." Obesity Research (2001); 9.4: 264-267.
Hanley, Michael J., et al. "Effect of obesity on the pharmacokinetics of drugs in humans." Clinical Pharmacokinetics (2010); 49.2: 71-87.
Laederach-Hofmann, Kurt, et al. "Links between body mass index, total body fat, cholesterol, high-density lipoprotein, and insulin sensitivity in patients with obesity related to depression, anger, and anxiety." International Journal of Eating Disorders (2002); 32.1: 58-71.
McElroy, Susan L., et al. "Are mood disorders and obesity related? A review for the mental health professional." J Clin Psychiatry (2004); 65.5: 634-651.
PCT/US2017/025131, International Search Report and Written Opinion, dated Jun. 27, 2017, 15 pages.
Trintellix (vortioxetine), "Highlights of Prescribing Information", Label, Reference ID: 4067968, Distributed and marketed by Takeda Pharmaceuticals America, Inc., Deerfield, IL and Lundbeck, Deerfield, IL, © 2013-2017 Takeda Pharmaceuticals America, Inc.; Initial U.S. Approval: 2013, Revised: Mar. 2017 [retrieved Jun. 10, 2017]. Retrieved from the Internet https://www.accessdata.fda.gov/drugsatfda_docs/label/2017/204447s009lbl.pdf], 29 pages.

*Primary Examiner* — Jeffrey S Lundgren
*Assistant Examiner* — William Y Lee
(74) *Attorney, Agent, or Firm* — Cooley LLP

(57) ABSTRACT

The present disclosure relates to methods of transitioning patients or obese patients being treated with vortioxetine to treatment with a monoamine oxidase inhibitor (MAOI). The methods provided include delaying administration of the MAOI for certain time periods after stopping administration of vortioxetine. The patients or obese patients possess various capabilities of metabolizing vortioxetine. The current disclosure also includes methods of switching patients to a MAOI intended to treat psychiatric disorders while being treated with vortioxetine. The methods disclosed further comprise determining vortioxetine plasma clearance and washout time for patients with different body fat status and/or different CYP2D6 metabolizer status.

16 Claims, 7 Drawing Sheets

METHODS OF TREATING DEPRESSION

CROSS-REFERENCE TO RELATED APPLICATIONS

This application is a continuation-in-part application of U.S. patent application Ser. No. 15/474,675, filed on Mar. 30, 2017, the disclosure of which is hereby incorporated by reference in its entirety for all purposes.

BACKGROUND

Selective serotonin reuptake inhibitors (SSRIs) are a class of drugs that are used for treating various depression and anxiety related disorders. Vortioxetine, also called Brintellix or Trintellix is a SSRI that is used for treating major depressive disorders. Vortioxetine can function as a serotonin modulator and stimulator, which can antagonize post-synaptic serotonin receptors and inhibit the reuptake of serotonin, and therefore can increase the availability of serotonin in the synaptic cleft and in the system. Patients with major depressive disorders who are treated with vortioxetine for a period of time may require that treatment with vortioxetine be replaced with treatment with monoamine oxidase inhibitors (MAOIs), which can also elevate the levels of serotonin. MAOIs can be used as the primary treatment if vortioxetine is not effective in certain patients.

However, when using vortioxetine, switching a patient to an MAOI may elevate the serotonin levels too much and may greatly increase the patient's risks of developing serotonin syndrome, or serotonin toxicity, for which there is no antidote, and which can be life threatening or fatal if not monitored carefully. Recent statistics from the Toxic Exposure Surveillance System (TESS) show that approximately 17% of the reported SSRI exposures result in moderate to severe outcomes, including 103 deaths in 2004 and 118 deaths in 2005. In some cases, the risks of transitioning from treatment with vortioxetine to an MAOI may be perceived as so severe that a physician may not even attempt treatment with vortioxetine in case a transition to treatment with an MAOI may be required.

Because there is no treatment available for serotonin syndrome, precautions for the transition from vortioxetine to MAOIs are especially important. According to the drug label for vortioxetine provided by the manufacturer, the recommendation washout period for patients who switch to MAOIs from vortioxetine is a wait of at least 21 days. However, this recommendation presumes that every patient requires the same washout period and may overlook that certain patient populations may require different washout periods when transitioning from vortioxetine to an MAOI.

The present applicants have discovered that certain patient populations or subpopulations are at higher risk of developing serotonin syndrome when transitioning from treatment with vortioxetine to MAOIs than was previously known, based on specific physiological characteristics, as described herein. The present disclosure describes new methods for addressing the risks of serotonin syndrome in such populations or subpopulations.

SUMMARY OF THE INVENTION

The present disclosure provides methods of treating a major depressive disorder in a patient with vortioxetine, wherein after treating the patient with vortioxetine, administration of vortioxetine is stopped, and the patient is subsequently treated with a monoamine oxidase inhibitor (MAOI).

Applicants have discovered that although vortioxetine is presently considered safe, even for patients with poor and intermediate CYP2D6 enzyme function (i.e., "poor and intermediate CYP2D6 metabolizers"), patients with specific physiological characteristics as described herein experience a substantially greater exposure to vortioxetine than previously known, and therefore after ceasing administration of vortioxetine, require substantially longer "washout" periods prior to starting administration of an MAOI in order to reduce the risk of serotonin syndrome to acceptable levels. More specifically, the present applicants have found that while all drugs exhibit some level of variability in exposure among different patients, previously unknown linkages between body fat and elimination half-life result in substantially higher than anticipated vortioxetine exposure in some patient populations as described herein. In addition, even patients with e.g., BMI values in the "normal" range (about 18.5-24.9) can exhibit substantially reduced vortioxetine elimination (e.g., as represented by elevated elimination half-life values compared to the mean terminal half-life of "approximately 66 hours" reported in section 12.3 of the TRINTELLIX label, revised March 2017) when the patient is an intermediate or poor CYP2D6 metabolizer. Thus, as disclosed herein, the present inventors have found that specific patient populations require substantially different and longer "washout" periods prior to starting administration of an MAOI intended to treat psychological disorders after treatment with vortioxetine.

In some embodiments, the methods comprise (a) stopping administration of vortioxetine and (b) delaying administration of the MAOI for more than 21 days after step (a). In one embodiment, the patient has BMI of at least about 35. In one embodiment, the patient has a % IBW of at least about 150%. In one embodiment, the patient has a waist size greater than about 42 inches. In one embodiment, the patient has a % body fat greater than about 40%. In another embodiment, the patient has a % android body fat greater than about 40%. In another embodiment, the patient has a % gynoid body fat greater than about 40%. In yet another embodiment, the patient has total body fat greater than about 40 kg. In other embodiments, the patient is an intermediate CYP2D6 metabolizer. In some embodiments, the patient is a poor CYP2D6 metabolizer.

In some embodiments, the delay period in step (b) is at least 4 weeks. In some embodiments, the patient has a BMI of at least about 40 or at least about 50. In some embodiments, the patient has a % IBW of at least about 250%. In some embodiments, the patient has a waist size greater than about 48 inches. In some embodiments, the patient has a body fat at least about 50%. In some embodiments, the patient has a % android body fat of at least about 50%. In some embodiments, the patient has a % gynoid body fat of at least about 50%. In some embodiments, the patient has a total body fat at least about 50 kg. In some embodiments, the patient is an intermediate CYP2D6 metabolizer. In some embodiments, the patient is a poor CYP2D6 metabolizer.

The present disclosure also provides methods of transitioning a patient being treated with vortioxetine to treatment with a monoamine oxidase inhibitor (MAOI) for treatment of a psychological disorder. In some embodiments, the methods comprise (a) stopping administration of vortioxetine and (b) delaying administration of the MAOI after step (a). In some embodiments, the time period of delaying administration is at least 7.5 times the average $t_{1/2}$ of vortioxetine in obese patients.

In one embodiment, the patient has a BMI of at least about 35. In one embodiment, the patient has a % ideal body weight (IBW) of at least about 150%. In one embodiment, the patient has a waist size greater than about 42 inches. In one embodiment, the obese patient has a body fat greater than about 40%. In another embodiment, the obese patient has a % android body fat greater than about 40%. In another embodiment, the obese patient has a % gynoid body fat greater than about 40%. In yet another embodiment, the obese patient has total body fat greater than about 40 kg.

In some embodiments, the delay period in step (b) is for at least 7.5 times the maximum $t_{1/2}$ of vortioxetine in patients having one or more of the physiological characteristics described herein. In some embodiments, the delay period in step (b) is more than 21 days. In some embodiments, the patient has a BMI of at least about 40 or at least about 50. In some embodiments, the patient has a % IBW of at least about 250%. In some embodiments, the patient has waist size greater than about 48 inches. In some embodiments, the patient has a body fat at least about 50%. In some embodiments, the patient has a % android body fat of at least about 50%. In some embodiments, the patient has a % gynoid body fat of at least about 50%. In some embodiments, the patient has a total body fat at least about 50 kg. In some embodiments, the patient is an intermediate CYP2D6 metabolizer. In some embodiments, the patient is a poor CYP2D6 metabolizer.

The present disclosure also provides methods for transitioning a patient being treated with vortioxetine and having one or more of the physiological characteristics described herein, to treatment with a monoamine oxidase inhibitor (MAOI). In some embodiments, the methods comprise (a) stopping administration of vortioxetine and (b) delaying administration of the MAOI after step (a). In some embodiments, the time required for delaying administration is at least the time required for the average washout plasma level of the patient having the physiological characteristics described herein to be equivalent to the 21 day plasma level of a normal patient.

In one embodiment, the patient has a BMI of at least about 35. In one embodiment, the patient has a % ideal body weight (IBW) of at least about 150%. In one embodiment, the patient has a waist size greater than about 42 inches. In one embodiment, the patient has a % body fat greater than about 40%. In another embodiment, the patient has a % android body fat greater than about 40%. In another embodiment, the patient has a % gynoid body fat greater than about 40%. In yet another embodiment, the patient has a total body fat greater than about 40 kg.

In some embodiments, the delay period in step (b) is for at least the time required for the maximum washout plasma level of a patient having at least one of the physiological characteristics described herein to be equivalent to the 21 day plasma level normal patient. In some embodiments, the 21 day plasma level of the normal patient is the 21 day plasma level of a normal patient administered a daily dose of 20 mg vortioxetine and exhibiting a $t_{1/2}$ of about 66 hours. In some embodiments, the 21 day plasma level of the normal patient is the 21 day plasma level of a normal patient administered a daily dose of 10 mg vortioxetine and exhibiting a $t_{1/2}$ of about 66 hours. In other embodiments, the 21 day plasma level of the normal patient is the 21 day plasma level of a normal patient administered a daily dose of 5 mg vortioxetine and exhibiting a $t_{1/2}$ of about 66 hours.

In some embodiments, the delay period in step (b) is more than 21 days. In some embodiments, the patient has a BMI of at least about 40 or at least about 50. In some embodiments, the patient has a % IBW of at least about 250%. In some embodiments, the patient has waist size greater than about 48 inches. In some embodiments, the patient has a % body fat at least about 50%. In some embodiments, the patient has a % android body fat of at least about 50%. In some embodiments, the patient has a % gynoid body fat of at least about 50%. In some embodiments, the patient has a total body fat at least about 50 kg. In some embodiments, the patient is an intermediate CYP2D6 metabolizer. In some embodiments, the patient is a poor CYP2D6 metabolizer.

The present disclosure also provides methods of transitioning a patient being treated with vortioxetine to treatment with a monoamine oxidase inhibitor (MAOI). In some embodiments, the methods comprise (a) stopping administration of vortioxetine and (b) delaying administration of the MAOI after step (a). In some embodiments, the time required for delaying administration is at least about 7.5× estimated $t_{1/2}$ of vortioxetine, calculated by: estimated vortioxetine $t_{1/2}$=1.025 (total body fat in kg)+17.3 (steady-state vortioxetine plasma concentration in ng/mL)−55.4. Applicants note that the steady-state plasma level of vortioxetine is essentially linear with dose, and the term "steady-state vortioxetine plasma concentration in ng/mL" as used in the above equation refers to the steady-state plasma concentration of vortioxetine normalized to a 5 mg dose. In other words, in order to estimate the delay time for a patient administered a 10 mg dose of vortioxetine using the above equation, the measured steady-state plasma level for that patient can be divided by 2 in order to obtain the steady-state plasma concentration value normalized to a dose of 5 mg. Similarly, for patients administered 15 mg or 20 mg of vortioxetine, the steady state value normalized to a 5 mg dose is obtained by dividing the measured steady-state plasma level of vortioxetine by 3 or 4, respectively. Further, for the patients described herein, who have high levels of body fat and/or who are intermediate or worse (e.g., poor) metabolizers, the minimum estimated $t_{1/2}$ value calculated using the above equation is greater than 66 hours because such patients have steady-state plasma levels (normalized to that of a 5 mg vortioxetine dose) and/or total body fat levels such that the estimated $t_{1/2}$ using the above equation is greater than 66 hours. In one embodiment, the patient has a total body fat of at least 43 kg.

Alternatively, the appropriate delay time can be determined by estimating the time required to achieve the same plasma level as a patient with normal weight and normal CYP2D6 metabolizer status (i.e., extensive CYP2D6 metabolizers) taking the same vortioxetine dose, 21 days after stopping the vortioxetine dose. The time required to obtain the "21 day equivalency" plasma level of such a "normal" patient would provide the same degree of safety—or alternatively stated, the same degree of risk—of serotonin syndrome. In order to do so, the estimated $t_{1/2}$ calculated as above for an obese and/or intermediate/poor CYP2D6 metabolizer can be used to calculate the delay time required for the steady-state vortioxetine plasma level of that patient to drop to the 21 day equivalent level of a patient with normal weight and normal CYP2D6 metabolizer status (i.e., extensive CYP2D6 metabolizers) taking the same vortioxetine dose.

In some embodiments, the patient having at least one of the physiological characteristics described herein has a steady-state vortioxetine plasma level ranging from about 1.4-10 ng/mL. In other embodiments, the patient has a steady-state vortioxetine plasma level ranging from about 11-16 ng/mL. In other embodiments, the patient has a steady-state vortioxetine plasma level greater than about 16 ng/mL. In some embodiments, the patient is an intermediate CYP2D6 metabolizer. In some embodiments, the obese patient is a poor CYP2D6 metabolizer.

In some embodiments, the patient has a total body fat ranging from about 43-104 kg. In some embodiments, when the total body fat is less than about 100 kg, the steady-state plasma concentration is at least about 6 ng/mL. In other embodiments, when the steady-state plasma concentration is less than about 6 ng/mL, the total body fat is at least about 100 kg.

In some embodiments, the patient is an extensive CYP2D6 metabolizer with a total body fat of about 60 kg or more, wherein the estimated half-life based on average steady vortioxetine plasma levels is about 70 hours or more. In some embodiments, the patient is an extensive CYP2D6 metabolizer with a total body fat of about 40 kg or more, wherein the estimated half-life based on the highest steady vortioxetine plasma levels of that population is about 70 hours or more. In other embodiments, the patient is an intermediate or poor CYP2D6 metabolizer with a total body fat of about 10 kg or more, wherein the estimated half-life based on average or highest steady vortioxetine plasma levels in that population is about 100 hours or more. In still another embodiment, the patient is a poor CYP2D6 metabolizer with a total body fat of about 10 kg or more, wherein the estimated half-life based on average steady vortioxetine plasma levels is about 200 hours or more.

In some embodiments, the first dose of MAOI is administered at a time after step (b) which is determined by the following equation: $T_{1/2}$=percent increase in half-life of vortioxetine+504 h, wherein the percent increase in half-life is [(half-life of vortioxetine in the patient—an average half-life of vortioxetine in a normal patient)/the average half-life of vortioxetine in the normal patient]*100. In some embodiments, the average half-life of vortioxetine in the normal patient is 54 h.

In some embodiments, the first dose of MAOI is administered at a time after step (b) which is determined by the following equation: $T_{1/2}$=(half-life of vortioxetine in the patient/the average half-life of vortioxetine in a normal patient)*504 h. In some embodiments, the average half-life of vortioxetine in the normal patient is 54 h.

In some embodiments, the first dose of MAOI is administered at a time after step (b) which is determined by the following equation: $T_{1/2}$=[(Ln 2)×$V_d$×$C_{ss}$/(5 mg/day)]*7.5, wherein Ln 2 is the natural logarithm of 2, $V_d$ is a volume distribution of vortioxetine in the patient, and $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5× [0.00213 ($C_{ss}$×the patient's body weight in pounds)+0.94], wherein $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5×[0.644 ($C_{ss}$×the patient's waist circumference in inches)+0.013], wherein $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5 [0.01388×($C_{ss}$×the patient's BMI)+0.879], wherein $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5 [0.00766×($C_{ss}$×the patient's total android fat in kilograms)+1.33], wherein $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5 [0.0108×($C_{ss}$×the patient's percent android fat)+0.7668], wherein $C_{ss}$ is a predicted steady-state plasma vortioxetine concentration in the patient (in ng/mL).

In some embodiments, the first dose of MAOI is administered at a time after step (b) which is determined by the following equation: $T_{1/2}$=7.5 [0.00298×($C_{ss}$×the patient's percent ideal body weight in pounds)+0.8722, wherein $C_{ss}$ is a predicted steady-state plasma vortioxetine concentration in the patient (in ng/mL) and percent ideal body weight is [(the patient's body weight×100)/ideal body weight)].

In some embodiments, the first dose of MAOI is administered at a time which is at least about 31 days after step (b). In other embodiments, the first dose of MAOI is administered at a time which is in the range of from about 24 days to about 60 days after step (b), e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 days, inclusive of all values and subranges therebetween. In other embodiments, the first dose of MAOI is administered at a time which is in the range of about 30 to about 35 days after step (b). In other embodiments, the first dose of MAOI is administered at a time which is about 31 days after step (b). In other embodiments, the first dose of MAOI is administered at a time which is about 32 days after step (b).

BRIEF DESCRIPTION OF THE FIGURE

FIG. 6A. represents the linear concentration axis and FIG. 6B represents the logarithmic concentration axis.

FIG. 9A: Washout $T_{1/2}$=0.00213 ($C_{ss} \times$weight)+0.94; FIG. 9B: Washout $T_{1/2}$=0.644 ($C_{ss} \times$ waist circumference)+0.013.

DETAILED DESCRIPTION

Figure 1:
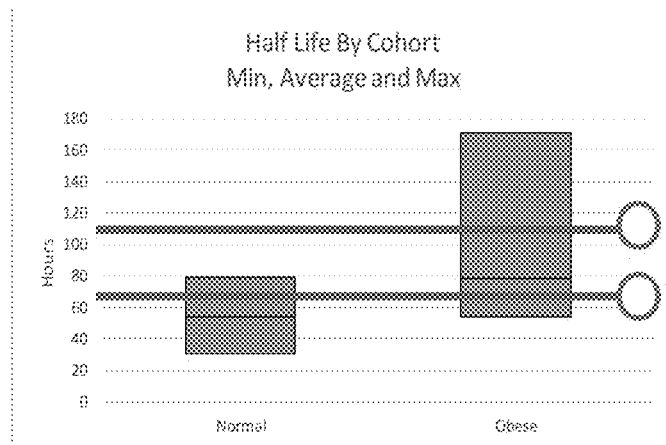
FIG. 1 is a comparison of the distribution of elimination half-life values of vortioxetine for obese patients (BMI>35) and normal patients (BMI<25). The lower horizontal line corresponds to the 66 hour $t_{1/2}$ stated in the Trintellix label, and the upper horizontal line represents a 110 hour $t_{1/2}$.

Disclosed herein are methods of treating a major depressive disorder in a patient with vortioxetine, wherein after treating the patient with vortioxetine, administration of vortioxetine is stopped, and the patient being treated with vortioxetine, particularly patients having one or more of the physiological characteristics described herein is subsequently treated with a MAOI. Methods of transitioning or switching patients to a MAOI intended to treat psychiatric disorders are also described herein. The present disclosure also provides methods of preventing or decreasing the risk of serotonin syndrome in patients or obese patients switching from vortioxetine to MAOIs (including those for treating psychiatric disorders). Additionally, it provides methods for such a transition in patients that are not obese but are intermediate or worse CYP2D6 metabolizers.

Serotonin, or 5-hydroxytryptamine, can be enzymatically synthesized from tryptophan with tryptophan hydroxylase and other metabolizing enzymes. In the central nervous system, neurotransmitters such as serotonin can be released by presynaptic neuron cells to the synaptic clefts. The released serotonin can then be in contact with postsynaptic neuron cells. The postsynaptic cells can release certain levels of serotonin, which can be taken up by the receptors on the presynaptic neuron cells. Maintaining adequate levels of serotonin can be critical for regulating mood and producing new brain cells. Therefore, the imbalance of serotonin metabolism may lead to depression and other psychiatric disorders. However, serotonin excess leads to symptoms similar to an ecstasy overdose, ranging from shivering and diarrhea to muscle rigidity, irregular heartbeat, fever, seizures, and loss of consciousness. Such severe symptoms can be fatal.

Selective serotonin reuptake inhibitors (SSRIs) are a class of drugs often indicated for the treatment of major depressive disorders (MDD) and anxiety disorders. Without wishing to be bound by theory, SSRIs can interact with neurotransmitters such as serotonin and may restrict the reuptake of serotonin by the presynaptic neuron cells, and thereby can elevate the levels of serotonin in synaptic clefts. Serotonin then remains in the synaptic cleft for a longer period of time and can stimulate the signaling between synaptic neuron cells.

In some embodiments, vortioxetine (i.e., Brintellix, Trintellix) can be indicated for the treatment of depressive disorders such as depression, major depressive disorder (MDD), pre-menstrual dysphoric disorder (PMDD), acute depressive episodes with bipolar I, treatment resistant depression, general anxiety disorder (GAD), obsessive compulsive disorder (OCD), panic disorder, post-traumatic stress disorder (PTSD), social anxiety disorder, bulimia nervosa, cognitive dysfunction in pre-menstrual dysphoric disorder, attention deficit hyperactivity disorder (ADHD), attention deficit hyperactivity disorder in adult patients, and combinations of any of the foregoing. In one embodiment, vortioxetine can be indicated for the treatment of MDD. In some embodiments, vortioxetine can be indicated for the treatment of anxiety related disorders. In one embodiment, vortioxetine can be indicated for the treatment of general anxiety disorder. In one embodiment, vortioxetine can be indicated for the treatment of panic disorder. In one embodiment, vortioxetine can be indicated for the treatment of post-traumatic stress disorder. In one embodiment, vortioxetine can be indicated for the treatment of social anxiety disorder. In one embodiment, vortioxetine can be indicated for the treatment of binge eating disorder. In some embodiments, vortioxetine can be indicated for the treatment of cognitive dysfunction in MDD. In some embodiments, vortioxetine can be indicated for the treatment of attention deficit hyperactivity disorders in patients. In other embodiments, vortioxetine can be used for treating menopausal depression, children and adolescents with depressive or anxiety disorder, and MDD in children and adolescents. In other embodiments, vortioxetine can be used as an adjunct to schizophrenia treatment.

In various embodiments, the use of MAOIs intended to treat psychiatric disorders with vortioxetine, or within 21 days of stopping treatment with vortioxetine is contraindicated because of an increased risk of serotonin syndrome. In various embodiments, patients with a BMI≥35 should wait at least 24.5 days after stopping treatment with vortioxetine before starting an MAOI. In various embodiments, exposure to vortioxetine is increased in patients with intermediate or worse (e.g., poor) CYP2D6 metabolizer status, thus, the use of MAOIs is contraindicated within 35 days of stopping treatment with vortioxetine. In various embodiments, patients with a BMI≥35 and intermediate or worse (e.g., poor) CYP2D6 metabolizer status should wait at least 42 days after stopping vortioxetine before starting an MAOI due to increased risk of serotonin syndrome.

In some embodiments, vortioxetine can be indicated for migraine headache prophylaxis. In some embodiments, vortioxetine can be indicated for the treatment of chronic daily headaches. In some embodiments, vortioxetine can be indicated for the treatment of premature ejaculation. In some embodiments, vortioxetine can be indicated for the treatment of diabetic neuropathy. In some embodiments, vortioxetine can be indicated for the treatment of fibromyalgia. In some embodiments, vortioxetine can be indicated for the treatment of neurocardiogenic syncope. In some embodiments, vortioxetine can be indicated for the treatment of social phobia. In some embodiments, vortioxetine can be indicated for the treatment of substance abuse dependence. In some embodiments, vortioxetine can be indicated for the treatment of autism. In some embodiments, vortioxetine can be indicated for the treatment of arthritis. In some embodiments, vortioxetine can be indicated for the treatment of deficits caused by stroke. In some embodiments, vortioxetine can be indicated for the treatment of irritable bowel syndrome. In some embodiments, vortioxetine can be indicated for the treatment of tinnitus. In some embodiments, vortioxetine can be indicated for the treatment of Tourette's syndrome.

In some embodiments, vortioxetine can be indicated for the treatment of corticosteroid-induced memory impairment. In some embodiments, vortioxetine can be indicated for the treatment of marijuana dependence. In some embodiments, vortioxetine can be indicated for the treatment of separation anxiety disorder. In some embodiments, vortioxetine can be indicated for the treatment of partial epilepsy. In some embodiments, vortioxetine can be indicated for the treatment of multiple system atrophy. In some embodiments, vortioxetine can be indicated for the treatment of pediatric body dysmorphic disorder. In some embodiments, vortioxetine can be indicated for the treatment of attenuated psychosis syndrome. In some embodiments, vortioxetine can be indicated for the treatment of cocaine use in cocaine and opioid addicts. In some embodiments, vortioxetine can be indicated for the treatment of depersonalization disorder.

In the present disclosure, in some embodiments, MAOIs can include Eldepryl (selegiline). In some embodiments, MAOIs can include Emsam (selegiline). In some embodiments, MAOIs can include Zelapar (selegiline). In some embodiments, MAOIs can include Azilect (rasagiline). In some embodiments, MAOIs can include Nardil (phenelzine). In some embodiments, MAOIs can include Parnate (tranylcypromine). In some embodiments, MAOIs can include Marplan (isocarboxazid). In other embodiments, MAOIs can include Linezolid. In other embodiments, MAOIs can include Methylene Blue.

In some embodiments, MAOIs can be indicated for the treatment of Parkinson's disease. In some embodiments, MAOIs can be indicated for the treatment of major depressive disorder. In some embodiments, MAOIs can be indicated for the treatment for depressed patients who are clinically characterized as atypical, non-endogenous, and/or neurotic. In some embodiments, MAOIs can be indicated for the treatment of major depressive episode without Melancholia. In some embodiments, MAOIs can be indicated for the treatment of panic disorder. In some embodiments, MAOIs can be indicated for the treatment of generalized anxiety disorder. In some embodiments, MAOIs can be indicated for the treatment of phobias. In some embodiments, MAOIs can be indicated for the treatment of post-traumatic stress disorder. In some embodiments, MAOIs can be indicated for the treatment of migraine headaches resistant to other therapies. In some embodiments, MAOIs can be indicated for smoking cessation. In other embodiments, MAOIs can be indicated for the treatment of antibiotic resistance. In other embodiments, MAOIs can be indicated for the treatment of methemoglobinemia. In other embodiments, MAOIs can be indicated for the aid of visualization.

In some embodiments, more than about 21 days, at least about 21.5 days, at least about 22 days, at least about 22.5 days, at least about 23 days, at least about 23.5 days, at least about 24 days, at least about 24.5 days, at least about 25 days, at least about 25.5 days, at least about 26 days, at least about 26.5 days, at least about 27 days, at least about 27.5 days, at least about 28 days, at least about 28.5 days, at least about 29 days, at least about 29.5 days, at least about 30 days, at least about 30.5 days, at least about 31 days, at least about 31.5 days, at least about 32 days, at least about 32.5 days, at least about 33 days, at least about 33.5 days, at least about 34 days, at least about 34.5 days, at least about 35 days, at least about 35.5 days, at least about 36 days, at least about 36.5 days, at least about 37 days, at least about 37.5 days, at least about 38 days, at least about 38.5 days, at least about 39 days, at least about 39.5 days, at least about 40 days, at least about 40.5 days, at least about 41 days, at least about 41.5 days, at least about 42 days, at least about 42.5 days, at least about 43 days, at least about 43.5 days, at least about 44 days, at least about 44.5 days, at least about 45 days, at least about 45.5 days, at least about 46 days, at least about 46.5 days, at least about 47 days, at least about 47.5 days, at least about 48 days, at least about 48.5 days, at least about 49 days, at least about 49.5 days, at least about 50 days, at least about 50.5 days, at least about 51 days, at least about 51.5 days, at least about 52 days, at least about 52.5 days, at least about 53 days, at least about 53.5 days, at least about 54 days, at least about 54.5 days, at least about 55 days, at least about 55.5 days, at least about 56 days, at least about 56.5 days, at least about 57 days, at least about 57.5 days, at least about 58 days, at least about 58.5 days, at least about 59 days, at least about 59.5 days, at least about 60 days, at least about 60.5 days, at least about 61 days, at least about 61.5 days, at least about 62 days, at least about 62.5 days, at least about 63 days, at least about 63.5 days, at least about 64 days, at least about 64.5 days, at least about 65 days, at least about 65.5 days, at least about 66 days, at least about 66.5 days, at least about 67 days, at least about 67.5 days, at least about 68 days, at least about 68.5 days, at least about 69 days, at least about 69.5 days, or at least about 70 days, inclusive of all ranges and subranges therebetween, should elapse between discontinuation of vortioxetine and initiation of treatment with an MAOI for patients having the physiological characteristics described herein, including any of the MAOIs disclosed herein.

This "delay" or waiting period between ceasing or stopping the administration of vortioxetine and initiating administration of an MAOI can equivalently be characterized as the time that elapses between stopping administration of vortioxetine and administering the first dose of an MAOI. The skilled artisan will recognize that additional doses of MAOI are typically administered subsequently, but the "delay" or "washout" period as described herein is the time that elapses between stopping administration of vortioxetine and the first dose that initiates administration with an MAOI.

In other embodiments, more than about 3 weeks, at least about 4 weeks, at least 5 weeks, at least 6 weeks, at least 7 weeks, at least 8 weeks, at least 9 weeks, or at least 10 weeks inclusive of all ranges and subranges therebetween, should elapse between discontinuation of vortioxetine and initiation of treatment with an MAOI for patients having the physiological characteristics described herein, including any of the MAOIs disclosed herein In some embodiments, after stopping treatment with vortioxetine, a time period equal to at least 7.5 half-lives, at least about 8 half-lives, at least about 8.5 half-lives, at least about 9 half-lives, inclusive of all ranges and subranges therebetween, of vortioxetine should elapse before starting therapy with the MAOI for patients having the physiological characteristics described herein, including any of the MAOIs disclosed herein.

According to the drug label (Takeda Pharmaceuticals, America, revised August 2016), vortioxetine contains the beta polymorph of vortioxetine hydrobromide. Current recommended dosing levels of vortioxetine are 10 mg/day as the starting dosage and increase to 20 mg/day. Alternatively, 5 mg/day may be used if higher doses are intolerable. Further, according to the drug label, the mean terminal half-life ($t_{1/2}$) of vortioxetine is about 66 hours and the steady-state plasma concentrations can be achieved within 2 weeks of dosing. The prescription of vortioxetine can include those described in the "Highlights of Prescribing Information" for vortioxetine provided by the drug manufacturers, Lundbeck and Takeda, in the TRINTELLIX label revised March 2017, which is incorporated herein by reference in its entirety for all purposes.

Monoamine oxidase inhibitors, similarly to SSRIs, can increase the levels of neurotransmitters including serotonin by inhibiting monoamine oxidases, which may be catabolizing enzymes of serotonin and other neurotransmitters. For instance, MAOIs can be administered as a second course of treatment after the treatment with vortioxetine to treat psychiatric disorders.

As used herein, "MAOI" refers to any drugs in the monoamine oxidase inhibitor class or similar drugs or treatments that may exert similar serotonergic effects when being used with SSRIs as described herein.

The presence of concomitant and clinically significant plasma levels of vortioxetine and MAOIs may synergistically increase the serotonin levels, it also creates the risks of inducing serotonin syndrome. Serotonin syndrome (e.g. serotonin toxicity, serotonin shock) may be generated due to excess serotonin buildup in the central nervous system and can be a life-threatening condition that does not have an antidote. As discussed above, some examples of serotonin syndrome symptoms may include, but are not limited to, increased heart rate, mental status changes, neuromuscular symptoms, shivering, seizures, and gastrointestinal syndromes. Since vortioxetine and MAOIs affect serotonin levels by different and independent biochemical mechanisms (synaptic uptake of serotonin, and monoamine oxidase inhibition), too rapid a transition from treatment with vortioxetine to treatment with an MAOI can result in clinically significant plasma levels of both drugs. As a result, serotonin clearance is inhibited by both biochemical mechanisms, rather than by a single biochemical mechanism when clinically significant levels of only one drug are present, resulting in excessive serotonin levels.

Due to the severity and irreversibility of serotonin syndrome, contraindications or washout periods are advised when transitioning to the use of MAOIs intended to treat psychiatric disorders from all SSRIs, including vortioxetine. As used herein, "contraindication" refers to a condition or factor that serves as a reason to withhold a certain medical treatment due to the harm that it would cause patients. The contraindications can range from 2 to 5 weeks in length. Alternatively, the contraindications can be 7.5 times the stated half-life of the SSRIs. In various embodiments, any of the methods of the present invention can include a step of advising a patient that use of an MAOI after treatment with vortioxetine, or after ceasing administration of vortioxetine for any of the delay or washout periods described herein, is contraindicated. In other embodiments, the methods of the present invention can include a step of advising a patient that one of the particular delay or washout periods (e.g., more than 21 days after stopping administration of vortioxetine) is appropriate, or alternatively that a shorter washout period is contraindicated, depending upon the patient's particular physiological characteristics as described herein.

For example, according to the drug label for vortioxetine (TRINTELLIX® label, revised August 2016), patients are advised to wait for at least 21 days after stopping vortioxetine before starting an MAOI intended to treat psychiatric disorders. However, the drug label of vortioxetine does not recognize that any stratification of the patient populations are required, and does not recognize the need to provide customized recommendations for washout periods related to the transition from vortioxetine to MAOIs for the particular patient populations identified herein.

The present disclosure provides methods for transitioning a patient, particularly patients with at least one of the physiological characteristics described herein, being treated with vortioxetine to treatment with a monoamine oxidase inhibitor. The physiological characteristics of patients that may require a more extended washout period prior to treatment with a MAOI includes reduced hepatic enzyme function, specifically reduced CYP2D6 enzyme function (such patients are characterized in the art as intermediate or poor CYP2D6 metabolizers), and/or a weight or body fat status variously characterized as described herein. In some embodiments, the patients can have various characteristics of body fat status. The term "body fat status," "body fat characteristics," "obese status," "obese characteristics," or other derivations or variations thereof refer to at least seven characteristics (BMI, % IBW, waist size, % body fat, % android fat, % gynoid fat, and total body fat) as described herein. In some embodiments, the body fat status may be referred to as obesity, and the patients may be referred to as obese, or obese patients.

As described herein, the present Applicants have found that certain classes of patients, i.e., patients having the particular physiological characteristics described herein such as body fat and weight status and/or hepatic metabolizing enzyme status, treated with vortioxetine, have substantially higher steady state plasma levels of vortioxetine, and/or exhibit a substantially longer elimination half-lives ($t_{1/2}$) of vortioxetine compared to those exhibited in "normal" patients—i.e., patients who do not exhibit the specific physiological characteristics described herein such as BMI of at least about 35, % IBW of at least about 150%, waist size greater than about 42 inches, % body fat greater than about 40%, % android body fat greater than about 40%, % gynoid body fat greater than about 40%, total body fat greater than about 40 kg, optionally in combination with impaired hepatic function, e.g., intermediate or poor CYP2D6 metabolizers. Alternatively, patients who are not obese (e.g., have any of the various measures of body fat status described herein which are not considered as indicative of obesity, such as a BMI less than about 35, % IBW of less than about 150%, waist size less than about 42 inches, % body fat less than about 40%, % android body fat less than about 40%, % gynoid body fat less than about 40%, or total body fat less than about 40 kg) but have impaired hepatic metabolic function, e.g., are considered intermediate or poor CYP2D6 metabolizers, have also been found by the present Applicants to have substantially higher steady state plasma levels of vortioxetine, and/or exhibit a substantially longer elimination half-lives ($t_{1/2}$) of vortioxetine compared to those exhibited in "normal" patients—i.e., patients who do not exhibit the specific physiological characteristics described herein. Such patients require a substantially longer washout period before transition to an MAOI compared to normal patients (e.g., non-obese patients with normal hepatic metabolizing enzyme function) to avoid adverse effects such as serotonin syndrome than has hitherto been recognized in the art. Conventionally, no such distinction between patients having such physiological characteristics has been recognized as requiring any change in "washout" periods between dosing with vortioxetine and MAOIs, as the effects of such physiological characteristics on steady state plasma levels of vortioxetine and/or elimination half-life was not previously known.

In a meta-analysis of vortioxetine population pharmacokinetics drawn from 26 clinical pharmacology studies, Areberg et al (*Basic & Clinical Pharmacology & Toxicology*, 2014, 115, 552-559) (incorporated herein in its entirety for all purposes) evaluated the effects of variables such as the patients' age, weight, body mass index (BMI), lean body mass (LBM), albumin, ALAT, ASAT, bilirubin, and creatinine clearance on the pharmacokinetics of vortioxetine. Areberg et al concluded that these variables are "of limited clinical relevance." Thus the conventional understanding is that BMI is itself not a clinically relevant parameter.

Vortioxetine can be metabolized primarily through oxidation via P450 isozymes such as CYP2D6. Alternatively, vortioxetine can be metabolized through oxidation via P450 isozymes such as CYP3A4/5, CYP2C9, CYP2C19, CYP2A6, CYP2C8, or CYP2B6. Each individual may have different activity levels of the P450 isozymes to metabolize vortioxetine. Categorizations of metabolizers may include, but are not limited to allelic heterogeneity in the P450 isozyme genes. For instance, the CYP2D6 gene can have allelic heterogeneity and its functionality (i.e., associated enzyme activity) can be categorized as full functionality, decreased functionality, and non-functionality. Further, CYP2D6 genotype can be categorized based on its metabolic status by using the "gene dose" method and can have the following scoring scale: (1) alleles with full functionality: a value of 1, (2) alleles with reduced functionality: a value of 0.5, and (3) alleles with no functionality: a value of 0. The identification of the metabolic status of CYP2D6 as disclosed herein includes those described in Areberg et al., (above), which is hereby incorporated by reference in its entirety for all purposes. The "normal" or typical patient has 2 normally functioning CYP2D6 alleles, and has full "normal" CYP2D6 enzyme functionality or activity and is referred to as an "extensive CYP2D6 metabolizer." Patients with one non-functional CYP2D6 allele and one normally functioning allele have reduced CYP2D6 enzyme function and are termed "intermediate CYP2D6 metabolizers." Patients with 2 non-functional CYP2D6 alleles have little or no CYP2D6 functionality or activity and are termed "poor CYP2D6 metabolizers."

The present disclosure also provides methods for transitioning a patient having one or more of the physiological characteristics as described herein, and/or a patient who is categorized as an intermediate CYP2D6 metabolizer or a poor CYP2D6 metabolizer, being treated with vortioxetine to treatment with a MAOI. As described herein, the present Applicants have found that obese patients, and/or patients who are intermediate or poor CYP2D6 metabolizers require substantially longer washout periods to clear vortioxetine in the system after stopping vortioxetine and before using a MAOI. No studies have reported that patients who have reduced CYP2D6 enzyme function need much longer washout periods than their counterparts who have normal CYP2D6 enzyme function (extensive metabolizers). For example, the report from the manufacturer of vortioxetine (as disclosed in Areberg et al., above) suggests that the mean elimination half-life of vortioxetine for all subjects is estimated as 65.8 hours, including intermediate and poor CYP2D6 metabolizers.

As used herein, the term "extensive CYP2D6 metabolizer" refers to a person who may have the gene dose for the CYP2D6 allele score of 1.5 or 2 and may have superior capabilities for metabolizing vortioxetine compared to his or her counterpart who is assigned as "intermediate CYP2D6 metabolizer" or "poor CYP2D6 metabolizer." As used herein, the term "intermediate CYP2D6 metabolizer" refers to a person who may have the gene dose for the CYP2D6 allele score of 0.5 to 1 and may have superior capabilities for metabolizing vortioxetine compared to his or her counterpart who is assigned as "poor CYP2D6 metabolizer." As used herein, the term "poor CYP2D6 metabolizer" refers to a person who may have the gene dose for the CYP2D6 allele score of 0 and may have the least capabilities for metabolizing vortioxetine compared to his or her counterpart who is assigned as an "intermediate metabolizer" or an "extensive metabolizer." In some embodiments, other suitable or conventional standards of categorizing CYP2D6 metabolizers may be used.

In some embodiments, the class of patients treated by the methods of the present disclosure have a body mass index (BMI; expressed in units of $kg/m^2$ unless otherwise specified) of at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, at least about 141, at least about 142, at least about 143, at least about 144, at least about 145, at least about 146, at least about 147, at least about 148, at least about 149, at least about 150, at least about 151, at least about 152, at least about 153, at least about 154, at least about 155, at least about 156, at least about 157, at least about 158, at least about 159, at least about 160, at least about 161, at least about 162, at least about 163, at least about 164, at least about 165, at least about 166, at least about 167, at least about 168, at least about 169, at least about 170, at least about 171, at least about 172, at least about 173, at least about 174, at least about 175, at least about 176, at least about 177, at least about 178, at least about 179, at least about 180, at least about 181, at least about 182, at least about 183, at least about 184, at least about 185, at least about 186, at least about 187, at least about 188, at least about 189, at least about 190, at least about 191, at least about 192, at least about 193, at least about 194, at least about 195, at least about 195, at least about 196, at least about 197, at least about 198, at least about 199, at least about 200, at least about 201, at least about 202, at least about 203, at least about 204, at least about 205, at least about 206, at least about 207, at least about 208, at least about 209, or at least about 210, inclusive of all ranges and subranges therebetween, and any BMI described herein. In one embodiment, the patient has a body mass index (BMI) of at least about 35. In another embodiment, the patient has a body mass index (BMI) of at least about 40. In another embodiment, the patient has a body mass index (BMI) of at least 50.

In some embodiments, a patient treated according to the methods of the present invention has a BMI of at least about 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be termed overweight or pre-obese. In some embodiments, a patient with a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween can be considered obese. In some embodiments, a patient with a BMI of at least about 35 to at least about 39.9, at least about 35.5 to at least about 39, at least about 36 to at least about 38.5, at least about 36.5 to at least about 38, or at least about 37 to at least about 37.5, inclusive of all ranges and subranges therebetween, and any BMI described herein, can be considered obese. In other embodiments, a patient treated by the methods of the present disclosure has a BMI of at least about 35 or more, 40 or more, 50 or more, 60 or more, 70 or more, 80 or more, 90 or more, 100 or more, 110 or more, 120 or more, 130 or more, 140 or more, 150 or more, 160 or more, 170 or more, 180 or more, 190 or more, 200 or more, or 210 or more, inclusive of all ranges and subranges therebetween. In some embodiments, the patient treated by the methods of the present disclosure can be an adult human. In other embodiments, the patient can be a male human. In still other embodiments, the patient can be a female human.

In some embodiments, the patient treated according to the methods of the present disclosure is a child or an adolescent with a BMI of at least about the $85^{th}$ percentile to at least about $95^{th}$ percentile, at least about the $86^{th}$ percentile to at least about $94^{th}$ percentile, at least about the $87^{th}$ percentile to at least about $93^{th}$ percentile, at least about the $88^{th}$ percentile to at least about $92^{th}$ percentile, at least about the $89^{th}$ percentile to at least about $90^{th}$ percentile, inclusive of all ranges and subranges therebetween, can be considered overweight or pre-obese. In some embodiments, the patient is a patient with a BMI of at least about the $95^{th}$ percentile, at least about $96^{th}$ percentile, at least about the $97^{th}$ percentile, at least about $98^{th}$ percentile, at least about $99^{th}$ percentile, or at least about $100^{th}$ percentile, inclusive of all ranges and subranges therebetween, and any BMI percentile described herein, and can be considered obese. In one embodiment, the patient is about 5 to about 19 years old or about 7 to about 18 years old.

In some embodiments, the patient treated according to the methods of the present disclosure is a female patient in the first trimester through third trimester of a pregnancy and has a BMI of at least 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be considered overweight or pre-obese. In some embodiments, the patient is a female patient in the first trimester through third trimester of a pregnancy and has a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween, and can be considered obese. In some embodiments, the patient treated according to the methods of the present invention is a female patient in the first trimester through third trimester of a pregnancy and has a BMI of at least about 35 to at least about 39.9, at least about 35.5 to at least about 39, at least about 36 to at least about 38.5, at least about 36.5 to at least about 38, at least about 37 to at least about 37.5, inclusive of all ranges and subranges therebetween, and can be considered severely obese.

In some embodiments, methods of calculating BMI may include, but are not limited to body weight in kilogram/(height in meters)$^2$, body weight in pounds/(height in inches)$^2$]×703, and the like.

In some embodiments, the patient treated according to the methods of the present disclosure can alternatively be described as having a % ideal body weight (% IBW) of at least about 110%, at least about 111%, at least about 112%, at least about 113%, at least about 114%, at least about 115%, at least about 116%, at least about 117%, at least about 118%, at least about 119%, at least about 120%, at least about 121%, at least about 122%, at least about 123%, at least about 124%, at least about 125%, at least about 126%, at least about 127%, at least about 128%, at least about 129%, at least about 130%, at least about 131%, at least about 132%, at least about 133%, at least about 134%, at least about 135%, at least about 136%, at least about 137%, at least about 138%, at least about 139%, at least about 140%, at least about 141%, at least about 142%, at least about 143%, at least about 144%, at least about 145%, at least about 146%, at least about 147%, at least about 148%, at least about 149%, at least about 150%, at least about 151%, at least about 152%, at least about 153%, at least about 154%, at least about 155%, at least about 156%, at least about 157%, at least about 158%, at least about 159%, at least about 160%, at least about 161%, at least about 162%, at least about 163%, at least about 164%, at least about 165%, at least about 166%, at least about 167%, at least about 168%, at least about 169%, at least about 170%, at least about 171%, at least about 172%, at least about 173%, at least about 174%, at least about 175%, at least about 176%, at least about 177%, at least about 178%, at least about 179%, at least about 180%, at least about 181%, at least about 182%, at least about 183%, at least about 184%, at least about 185%, at least about 186%, at least about 187%, at least about 188%, at least about 189%, at least about 190%, at least about 191%, at least about 192%, at least about 193%, at least about 194%, at least about 195%, at least about 196%, at least about 197%, at least about 198%, at least about 199%, at least about 200%, at least about 201%, at least about 202%, at least about 203%, at least about 204%, at least about 205%, at least about 206%, at least about 207%, at least about 208%, at least about 209%, at least about 210%, at least about 211%, at least about 212%, at least about 213%, at least about 214%, at least about 215%, at least about 216%, at least about 217%, at least about 218%, at least about 219%, at least about 220%, at least about 221%, at least about 222%, at least about 223%, at least about 224%, at least about 225%, at least about 226%, at least about 227%, at least about 228%, at least about 229%, at least about 230%, at least about 231%, at least about 232%, at least about 233%, at least about 234%, at least about 235%, at least about 236%, at least about 237%, at least about 238%, at least about 239%, at least about 240%, at least about 241%, at least about 242%, at least about 243%, at least about 244%, at least about 245%, at least about 246%, at least about 247%, at least about 248%, at least about 249%, at least about 250%, at least about 251%, at least about 252%, at least about 253%, at least about 254%, at least about 255%, at least about 256%, at least about 257%, at least about 258%, at least about 259%, at least about 260%, at least about 261%, at least about 262%, at least about 263%, at least about 264%, at least about 265%, at least about 266%, at least about 267%, at least about 268%, at least about 269%, at least about 270%, at least about 271%, at least about 272%, at least about 273%, at least about 274%, at least about 275%, at least about 276%, at least about 277%, at least about 278%, at least about 279%, or at least about 280%, inclusive of all ranges and subranges therebetween, and any % ideal body weight described herein. In one embodiment, the patient has % ideal body weight (IBW) of at least about 150%. In one embodiment, the patient has % ideal body weight (IBW) of at least about 250%. In other embodiment, the patient has % IBW of at least 150% and can be considered obese.

In some embodiments, the patient treated according to the present disclosure can alternatively be described as having a waist size or waist circumference greater than about 32, greater than about 33, greater than about 34, greater than about 35 inches, greater than about 36, greater than about 37, greater than about 38, greater than about 39, greater than about 40, greater than about 41, greater than about 42, greater than about 43, greater than about 44, greater than about 45, greater than about 46, greater than about 47, greater than about 48, greater than about 49, greater than about 50, greater than about 51, greater than about 52, greater than about 53, greater than about 54, greater than about 55, greater than about 56, greater than about 57, greater than about 58, greater than about 59, greater than about 60 inches, greater than about 61 inches, greater than about 62 inches, greater than about 63 inches, greater than about 64 inches, greater than about 65 inches, inclusive of all ranges and subranges therebetween, and any waist size or circumference described herein. In one embodiment, a patient having a waist size or waist circumference of about 42 inches can be considered obese. In another embodiment, the patient has waist size or waist circumference greater than about 48 inches. In other embodiment, the patient has waist or waist circumference of at least 42 inches.

In some embodiments, the patient treated according to the methods of the present disclosure can alternatively be described as having a % body fat greater than about 20%, greater than about 21%, greater than about 22%, greater than about 23%, greater than about 24%, greater than about 25%, greater than about 26%, greater than about 27%, greater than about 28%, greater than about 29%, greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, or greater than about 50%, inclusive of all ranges and subranges therebetween, and any % body fat described herein. In one embodiment, the patient has a body fat greater than about 40%. In one embodiment, the patient has a % body fat of at least about 50%. In another embodiment, a patient having a % body fat greater than about 40% can be considered obese. In some embodiments, methods of calculating % body fat can include, but are not limited to total body fat expressed as a percentage of total body weight. Other standards for obesity can be used. For example, the American Council on Exercise suggests that an "average" percentage of body fat for women is about 25-31%, and for men, about 18-24%, and for obese women, about 32% and higher, and obese men, about 25% and higher.

In other embodiments, the patient can alternatively be described as having a % android body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % android body fat described herein. In one embodiment, a patient having a % android body fat greater than about 40% can be considered obese. In one embodiment, a patient having a % android body fat greater than about 50% can be considered obese In other embodiments, the patient can alternatively be described as having a % android body fat of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%, inclusive of all ranges and subranges therebetween, and % android body fat described herein. In one embodiment, the patient has % android body fat of at least about 50%.

In other embodiments, the patient can alternatively be described as having a % gynoid body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % gynoid body fat described herein. In one embodiment, a patient having a % gynoid body fat greater than about 40% can be considered obese. In one embodiment, a patient having a % gynoid body fat greater than about 50% can be considered obese.

In other embodiments, the patient can alternatively be described as having a total body fat content greater than about 30 kg, greater than about 31 kg, greater than about 32 kg, greater than about 33 kg, greater than about 34 kg, greater than about 35 kg, greater than about 36 kg, greater than about 37 kg, greater than about 38 kg, greater than about 39 kg, greater than about 40 kg, greater than about 41 kg, greater than about 42 kg, greater than about 43 kg, greater than about 44 kg, greater than about 45 kg, greater than about 46 kg, greater than about 47 kg, greater than about 48 kg, greater than about 49 kg, greater than about 50 kg, greater than about 51 kg, greater than about 52 kg, greater than about 53 kg, greater than about 54 kg, greater than about 55 kg, greater than about 56 kg, greater than about 57 kg, greater than about 58 kg, greater than about 59 kg, greater than about 60 kg, greater than about 61 kg, greater than about 62 kg, greater than about 63 kg, greater than about 64 kg, greater than about 65 kg, greater than about 66 kg, greater than about 67 kg, greater than about 68 kg, greater than about 69 kg, greater than about 70 kg, greater than about 71 kg, greater than about 72 kg, greater than about 73 kg, greater than about 74 kg, greater than about 75 kg, greater than about 76 kg, greater than about 77 kg, greater than about 78 kg, greater than about 79 kg, greater than about 80 kg, greater than about 81 kg, greater than about 82 kg, greater than about 83 kg, greater than about 84 kg, greater than about 85 kg, greater than about 86 kg, greater than about 87 kg, greater than about 88 kg, greater than about 89 kg, greater than about 90 kg, greater than about 91 kg, greater than about 92 kg, greater than about 93 kg, greater than about 94 kg, greater than about 95 kg, greater than about 96 kg, greater than about 97 kg, greater than about 98 kg, greater than about 99 kg, greater than about 100 kg, at least 101 kg, at least 102 kg, at least 103 kg, at least 104 kg, at least 105 kg, at least 106 kg, at least 107 kg, at least 108 kg, at least 109 kg, or at least 110 kg, inclusive of all ranges and subranges therebetween, and any total body fat described herein. In one embodiment, a patient having total body fat greater than about 40 kg can be considered obese. In one embodiment, a patient having total body fat greater than about 50 kg can be considered obese.

In other embodiments, obesity status of patients treated with the methods of the present disclosure can be measured by waist-to-hip ratio. In other embodiments, obesity status of patients can be measured by skinfold thickness. In other embodiments, obesity status of patients can be measured by bioelectric impedance. In other embodiments, obesity status of patients can be measured by underwater weighing or densitometry. In other embodiments, the obesity status of patients can be measured by air-displacement plethysmography. In other embodiments, obesity status of patients can be measured by dilution method or hydrometry. In other embodiments, the obesity status of patients can be measured by dual energy X-ray absorptiometry. In other embodiments, the obesity status of patients can be measured by computerized tomography and magnetic resonance imaging. In some embodiments, the obesity status can be defined by, but is not limited to adopting the clinical standards, conventional standards, and/or the standards published by the World Health Organization and Center of Disease Control (both of which are herein incorporated by reference in their entireties for all purposes) when using the methods described herein. For example, the WHO defines an obese person as a person with a BMI of 30 or more, an overweight person is one with a BMI equal to or more than 25 (to less than 30). Similarly, the CDC defines normal as a BMI of 18.5 to less than 25, 25.0 to less than 30 as overweight, and 30.0 or higher as obese. The CDC further subdivides obesity into 3 classes: Class 1, a BMI of 30 to less than 35; Class 2, a BMI of 35 to less than 40; and Class 3, as a BMI of 40 or higher. The CDC sometimes refers to Class 3 obesity as "extreme" or "severe" obesity.

As used herein, the term "about" refers to an amount somewhat more or less than the stated parameter value, for example plus or minus five or ten percent of the object that "about" modifies, or as one of skill in the art would recognize from the context (e.g., approximately 50% of the interval between values). The term "about" also includes the value referenced. For example, a BMI of about 40 includes 40, as well as values somewhat below or above 40.

In some embodiments, the patient treated by the methods of the present disclosure can be characterized by two or more of the physiological characteristics described herein. For example the patient can have a BMI of at least about 35 and can have a % IBW of at least 150%. In some embodiments, the patient can have a BMI of at least about 35 and can have a waist size greater than about 42 inches. In some embodiments, the patient can have a BMI of at least about 35 and can have a % body fat greater than about 40%. In some embodiments, the patient can have a BMI of at least about 35 and can have a % android body fat greater than about 40%. In some embodiments, the patient can have a BMI of at least about 35 and can have a % gynoid body fat greater than about 40%. In some embodiments, the patient can have a BMI of at least about 35 and can have total body fat greater than about 40 kg. In various other embodiments, the patient can have any combination of two or more of any of the specific physiological parameters described herein.

In some embodiments, the patient can have three or more of the physiological parameters described herein, for example a BMI of at least about 35, a % IBW of at least 150%, and waist size greater than about 42 inches. In some embodiments, the patient can have a BMI of at least about 35, a % IBW of at least 150%, and a % body fat greater than about 40%. In some embodiments, the patient can have a BMI of at least about 35, a % IBW of at least 150%, and a % android body fat greater than about 40%. In some embodiments, the patient can have a BMI of at least about 35, a % IBW of at least 150%, and a % gynoid body fat greater than about 40%. In some embodiments, the patient can have a BMI of at least about 35, a % IBW of at least 150%, and total body fat greater than about 40 kg. In various other embodiments, the patient can have any combination of three or more of any of the specific physiological parameters described herein.

In some embodiments, the patient can have four or more of the physiological parameters described herein, for example the patient can have a BMI of at least about 35, a % IBW of at least 150%, waist size greater than about 42 inches, and a % body fat greater than about 40%. In some embodiments, the patient can have a BMI of at least about 35, a % IBW of at least 150%, waist size greater than about 42 inches, and a % android body fat greater than about 40%.

In some embodiments, the patient can have a BMI of at least about 35, a % IBW of at least 150%, waist size greater than about 42 inches, and a % gynoid body fat greater than about 40%. In some embodiments, the patient can have a BMI of at least about 35, a % IBW of at least 150%, a waist size greater than about 42 inches, and total body fat greater than about 43 kg. In some a embodiments, the patient can have a BMI of at least about 35, a % IBW of at least 150%, a waist size greater than about 42 inches, a % body fat greater than about 40%, and a % android body fat greater than about 40%. In some embodiments, the patient can have a BMI of at least about 35, a % IBW of at least 150%, a waist size greater than about 42 inches, a % body fat greater than about 40%, and a % gynoid body fat greater than about 40%. In some embodiments, the patient can have a BMI of at least about 35, a % IBW of at least 150%, a waist size greater than about 42 inches, a % body fat greater than about 40%, and total body fat greater than about 40 kg. In some embodiments, the patient can have a BMI of at least about 35, a % IBW of at least 150%, a waist size greater than about 42 inches, a % body fat greater than about 40%, a % android body fat greater than about 40%, in % gynoid body fat greater than about 40%, and total body fat greater than about 40 kg. In one embodiment, the patient who has a BMI of at least about 35, in % IBW of at least 150%, a waist size greater than about 42 inches, and a % body fat greater than about 40%, a % android body fat greater than about 40%, a % gynoid body fat greater than about 40%, and total body fat greater than about 40 kg. In various other embodiments, the patient can have any combination of any or all of the specific physiological parameters described herein. In still other embodiments, the patient can have a maximum vortioxetine $t_{1/2}$ of about 171 hours.

In some embodiments, the patient can have a waist size greater than about 42 inches, a body fat greater than about 40%, and a % android body fat greater than about 40%. In some embodiments, the patient can have a waist size greater than about 42 inches, a % body fat greater than about 40%, and a % gynoid body fat greater than about 40%. In some embodiments, the patient can have a waist size greater than about 42 inches, a % body fat greater than about 40%, and total body fat greater than about 40 kg.

In some embodiments, the patient can have a % body fat greater than about 40%, a android body fat greater than about 40%, and a % gynoid body fat greater than about 40%. In some embodiments, the patient can have a % body fat greater than about 40%, a % android body fat greater than about 40%, and total body fat greater than about 40 kg. In some embodiments, the patient can have a % body fat greater than about 40%, a % gynoid body fat greater than about 40%, and total body fat greater than about 40 kg. In some embodiments, a % android body fat greater than about 40%, and a % gynoid body fat greater than about 40%, and total body fat greater than about 43 kg. In some embodiments, the patient can have any combinations of obesity characteristics described herein In some embodiments, patients with at least one of the obesity characteristics described herein can be an intermediate CYP2D6 metabolizer. In other embodiments, the patients with at least one of the obesity characteristics described herein can be a poor CYP2D6 metabolizer. In some embodiments, the patients with at least one of the obesity characteristics described herein can be an extensive CYP2D6 metabolizer. In still other embodiments, the patient can have normal weight and be an intermediate or poor CYP2D6 metabolizer.

Alternatively, in some embodiments, the CYP2D6 genotype can be tested by using targeted variant analysis. In some embodiments, the CYP2D6 genotype can be tested by using sequence analysis of select exons.

The present disclosure also provides methods for switching patients to a monoamine oxidase (MAOI) intended to treat psychiatric disorders. In some embodiments, the methods contain (a) stopping administering vortioxetine and (b) delaying administration of the MAOI for more than 21 days. In some embodiments, the patient described herein has at least one of the physiological characteristics as described herein.

In some embodiments, the "washout" period or delay in the administration of the MAOI after cessation of treatment with vortioxetine to the patient can be more than about 21 days, more than about 22 days, more than about 23 days, more than about 24 days, more than about 25 days, more than about 26 days, more than about 27 days, more than about 28 days, more than about 29 days, more than about 30 days, more than about 31 days, more than about 32 days, more than about 33 days, more than about 34 days, more than about 35 days, more than about 36 days, more than about 37 days, more than about 38 days, more than about 39 days, more than about 40 days, more than about 41 days, more than about 42 days, more than about 43 days, more than about 44 days, more than about 45 days, more than about 46 days, more than about 47 days, more than about 48 days, more than about 49 days, more than about 50 days, more than about 51 days, more than about 52 days, more than about 53 days, more than about 54 days, more than about 55 days, more than about 56 days, more than about 57 days, more than about 58 days, more than about 59 days, more than about 60 days, more than about 61 days, more than about 62 days, more than about 63 days, more than about 64 days, more than about 65 days, more than about 66 days, more than about 67 days, more than about 68 days, more than about 69 days, more than about 70 days, inclusive of all ranges and subranges therebetween. In one embodiment, delaying the administration of the MAOI after cessation of vortioxetine is for more than 21 days. In some embodiments, delaying administration of the MAOI after cessation of vortioxetine can be for at least 3 weeks, at least 4 weeks, at least 5 weeks, at least 6 weeks, at least 8 weeks, at least 9 weeks, at least 10 weeks, inclusive of all ranges and subranges therebetween. In one embodiment, delaying administration of the MAOI after cessation of vortioxetine is for at least 4 weeks.

The present disclosure also provides methods of transitioning an obese patient (for example as defined by one or more of the physiological parameters described herein) being treated with vortioxetine to treatment with a MAOI intended to treat psychiatric disorders. In some embodiments, the methods comprise (a) stopping administering vortioxetine and (b) delaying administration of the MAOI after step (a) for a time or washout period as described herein. In some embodiments, the patient described herein has at least one of the physiological characteristics as described herein. In some embodiments, the time period for delaying administration of the MAOI after cessation of administering vortioxetine is at least 7.5 times the average $t_{1/2}$ of vortioxetine in patients having one or more of the physiological characteristics. In other embodiments, the delaying in step (b) is at least 21 days.

The present disclosure also provides methods for switching patients to a monoamine oxidase inhibitor (MAOI) intended to treat psychiatric disorders. In some embodiments, the methods contain (a) stopping administering vortioxetine and (b) delaying administration of the MAOI after step (a). In some embodiments, the patient described herein has at least one of the seven physiological characteristics as described above. In some embodiments, the time period for delaying administration of the MAOI after cessation of vortioxetine is at least 7.5 times the average $t_{1/2}$ of vortioxetine in obese patients. In other embodiments, the delaying in step (b) is at least 21 days.

In some embodiments, the delaying in step (b) can be more than about 21 days, at least about 22 days, at least about 23 days, at least about 24 days, at least about 25 days, at least about 26 days, at least about 27 days, at least about 28 days, at least about 29 days, at least about 30 days, at least about 31 days, at least about 32 days, at least about 33 days, at least about 34 days, at least about 35 days, at least about 36 days, at least about 37 days, at least about 38 days, at least about 39 days, at least about 40 days, at least about 41 days, at least about 42 days, at least about 43 days, at least about 44 days, at least about 45 days, at least about 46 days, at least about 47 days, at least about 48 days, at least about 49 days, at least about 50 days, at least about 51 days, at least about 52 days, at least about 53 days, at least about 54 days, at least about 55 days, at least about 56 days, at least about 57 days, at least about 58 days, at least about 59 days, or at least about 60 days, inclusive of all ranges and subranges therebetween. In one embodiment, the delaying in step (b) is more than 21 days.

In some embodiments, the average $t_{1/2}$ of vortioxetine in patients treated by the methods of the present disclosure can range from about 70 to 170 hours, including about 70 hours, about 75 hours, about 80 hours, about 85 hours, about 90 hours, about 95 hours, about 100 hours, about 105 hours, about 110 hours, about 115 hours, about 120 hours, about 125 hours, about 130 hours, about 135 hours, about 140 hours, about 145 hours, about 150 hours, about 155 hours, about 160 hours, about 165 hours, or about 170 hours, inclusive of all ranges and subranges therebetween. In particular embodiments, patients with a vortioxetine half-life greater than about 110 hours require a delay before administering an MAOI of at least about 5 weeks.

In various embodiments, a suitable washout period for patients according to the methods disclosed herein can be determined by multiplying the $t_{1/2}$ of the patient by 7.5. The $t_{1/2}$ can be determined using methods known in the art from the particular patient. Alternatively the $t_{1/2}$ can be estimated as described herein, for example by establishing the average or maximum $t_{1/2}$ for patients having the physiological characteristics described herein, and using the average or maximum $t_{1/2}$ as an estimate of the $t_{1/2}$ for patients with similar physiological characteristics (e.g., obese patients as described herein). Alternatively the estimated $t_{1/2}$ can be calculated based on specific physiological parameters as described herein.

Patients requiring a modified washout period in transitioning from vortioxetine to MAOI have one or more of the physiological characteristics described herein. For example, in one embodiment, the average $t_{1/2}$ of vortioxetine is at least about 79 hours in patients who have a BMI at least about 35. In some embodiments, the average $t_{1/2}$ is at least about 88 hours for patients who have a BMI of at least about 40. In some embodiments, the average $t_{1/2}$ of vortioxetine can be at least about 60 to 90 hours (e.g., about 60, about 65, about 70, about 75, about 80, about 85, or about 90 hours, inclusive of all ranges and subranges therebetween) in patients who have a BMI at least about 50. In one embodiment, the average $t_{1/2}$ of vortioxetine is at least about 89.5 hours in patients who have a BMI at least about 50. In some embodiments, the average $t_{1/2}$ of vortioxetine can be about 50 to 65 hours in patients who have BMI less than at least about 25 (e.g., "normal" patients). In one embodiment, the average $t_{1/2}$ of vortioxetine is about 54 hours in patients who have a BMI less than about 25.

In some embodiments, the average $t_{1/2}$ of vortioxetine can be at least about 80 to 92 hours (e.g., about 80, about 81, about 82, about 83, about 84, about 85, about 86, about 87, about 88, about 89, about 90, about 91, or about 92 hours, inclusive of all ranges and subranges therebetween) in patients who have a % IBW of at least about 250%. In one embodiment, the average $t_{1/2}$ of vortioxetine is at least about 90 hours in patients who have a % IBW of at least about 250%. In some embodiments, the average $t_{1/2}$ of vortioxetine can be about 55 to 70 hours in patients who have % IBW less than about 120% (e.g., "normal" patients). In one embodiment, the average $t_{1/2}$ of vortioxetine is at least about 62 hours in patients who have % IBW less than about 120%.

In some embodiments, the average $t_{1/2}$ of vortioxetine can be at least about 74 to 84 hours (e.g., about 74, about 75, about 76, about 77, about 78, about 79, about 80, about 81, about 82, about 83, or about 84, inclusive of all ranges and subranges therebetween) in patients who have a waist size greater than about 42 inches. In one embodiment, the average $t_{1/2}$ of vortioxetine is at least about 79 hours in patients who have a waist size greater than about 42 inches. In some embodiments, the average $t_{1/2}$ of vortioxetine can be at least about 84 to 94 hours (e.g., about 84, about 85, about 86, about 87, about 88, about 89, about 90, about 91, about 92, about 93, or about 94 hours, inclusive of all ranges and subranges therebetween) in patients who have a waist size greater than about 48 inches. In one embodiment, the average $t_{1/2}$ of vortioxetine is at least about 90 hours in patients who have a waist size greater than about 48 inches. In some embodiments, the average $t_{1/2}$ of vortioxetine can be about 46 to 56 hours in patients who have waist size less than about 38 inches (e.g., "normal" patients).

In some embodiments, the average $t_{1/2}$ of vortioxetine can be at least about 72 to 82 hours (e.g. about 72, about 73, about 74, about 75, about 76, about 77, about 78, about 79, about 80, about 81, or about 82 hours, inclusive of all ranges and subranges therebetween) in patients who have a % body fat greater than about 40%. In one embodiment, the average $t_{1/2}$ of vortioxetine is at least about 79 hours in patients who have a % body fat greater than about 40%. In some embodiments, the average $t_{1/2}$ of vortioxetine can be at least about 70 to 80 hours in patients who have a % body fat greater than about 50%. In one embodiment, the average $t_{1/2}$ of vortioxetine is at least about 77 hours in patients who have % body fat greater than about 50%.

In some embodiments, the average $t_{1/2}$ of vortioxetine can be more than about 66 to about 76 hours (e.g., more than about 66, about 67, about 68, about 69, about 70, about 71, about 72, about 73, about 74, about 75, or about 76 hours, inclusive of all ranges and subranges therebetween) in patients who have android body fat greater than about 40%. In one embodiment, the average $t_{1/2}$ of vortioxetine is at least about 74 hours in patients who have android body fat greater than about 40%. In some embodiments, the average $t_{1/2}$ of vortioxetine can be at least about 74 to 84 hours (e.g., about 74, about 75, about 76, about 77, about 78, about 79, about 80, about 81, about 82, about 83, or about 84 hours, inclusive of all ranges and subranges therebetween) in patients who have android body fat greater than about 50%. In one embodiment, the average $t_{1/2}$ of vortioxetine is at least about 79 hours in patients who have android body fat greater than about 50%.

In some embodiments, the average $t_{1/2}$ of vortioxetine in patients having the physiological characteristics described herein can be more than about 66 to about 74 hours (e.g., more than about 66, about 67, about 68, about 69, about 70, about 71, about 72, about 73, or about 74 hours, inclusive of all ranges and subranges therebetween) in patients who have gynoid body fat greater than about 40%. In one embodiment, the average $t_{1/2}$ of vortioxetine is at least about 70 hours in obese patients who have gynoid body fat greater than about 40%. In some embodiments, the average $t_{1/2}$ of vortioxetine can be at least about 74 to 84 hours (e.g., about 74, about 75, about 76, about 77, about 78, about 79, about 80, about 81, about 82, about 83, or about 84 hours, inclusive of all ranges and subranges therebetween) in patients who have gynoid body fat greater than about 50%. In one embodiment, the average $t_{1/2}$ of vortioxetine is at least about 79 hours in patients who have gynoid body fat greater than about 50%.

In some embodiments, the average $t_{1/2}$ of vortioxetine can be at least about 75 to 85 hours (e.g., about 75, about 76, about 77, about 78, about 79, about 80, about 81, about 82, about 83, about 84, or about 85 hours, inclusive of all ranges and subranges therebetween) in patients who have total body fat greater than about 40 kg. In one embodiment, the average $t_{1/2}$ of vortioxetine is at least about 79 hours in obese patients who have total body fat greater than about 40 kg. In some embodiments, the average $t_{1/2}$ of vortioxetine can be at least about 86 to 96 hours (e.g., about 86, about 87, about 88, about 89, about 90, about 91, about 92, about 93, about 94, about 95, or about 96 hours, inclusive of all ranges and subranges therebetween) in patients who have total body fat greater than about 50 kg. In one embodiment, the average $t_{1/2}$ of vortioxetine is at least about 94 hours in obese patients who have total body fat greater than about 50 kg. In some embodiments, the average $t_{1/2}$ of vortioxetine can be at least about 164 to 174 hours (e.g., about 164, about 165, about 166, about 167, about 168, about 169, about 170, about 171, about 172, about 173, or about 174 hours, inclusive of all ranges and subranges therebetween) in obese patients as described herein who are also intermediate CYP2D6 metabolizers. In one embodiment, the average $t_{1/2}$ of vortioxetine is at least about 171 hours in obese intermediate CYP2D6 metabolizers. In other embodiments, the average $t_{1/2}$ of vortioxetine can be at least more than about 66 to 75 hours and all ranges and subranges therebetween in non-obese intermediate CYP2D6 metabolizers. In one embodiment, the average $t_{1/2}$ of vortioxetine is at least about 72 hours in non-obese intermediate CYP2D6 metabolizers.

In some embodiments, a washout period of at least 7.5 times the average $t_{1/2}$ of vortioxetine in patients as described herein who have a BMI at least about 35 can be more than about 3 to 5 weeks, including more than about 3, about 4, or about 5 weeks, inclusive of all ranges and subranges therebetween. In one embodiment, 7.5 times the average $t_{1/2}$ of vortioxetine is at least about 4 weeks in patients who have a BMI at least about 35. In some embodiments, 7.5 times the average $t_{1/2}$ of vortioxetine can be more than about 3 to 5 weeks in patients who have a BMI at least about 50. In one embodiment, 7.5 times the average $t_{1/2}$ of vortioxetine is at least about 4 weeks in patients who have BMI at least about 50. In some embodiments, 7.5 times the average $t_{1/2}$ of vortioxetine can be more than about 3 to about 4 weeks in patients who have % IBW of at least about 150%. In one embodiment, 7.5 times the average $t_{1/2}$ of vortioxetine is more than about 3 weeks in patients who have a % IBW of at least about 150%. In some embodiments, 7.5 times the average $t_{1/2}$ of vortioxetine can be more than about 3 to about 5 weeks in patients who have a % IBW of at least about 250%. In one embodiment, 7.5 times the average $t_{1/2}$ of vortioxetine is at least about 4 weeks in patients who have % IBW of at least about 250%.

In some embodiments, 7.5 times the average $t_{1/2}$ of vortioxetine in patients as described herein can be more than about 3 to about 5 weeks in patients who have a waist size greater than about 42 inches. In one embodiment, 7.5 times the average $t_{1/2}$ of vortioxetine is more than about 3 weeks in patients who have a waist size greater than about 42 inches. In some embodiments, 7.5 times the average $t_{1/2}$ of vortioxetine can be more than about 3 to about 6 weeks in patients who have a waist size greater than about 48 inches. In one embodiment, 7.5 times the average $t_{1/2}$ of vortioxetine is at least about 4 weeks in patients who have a waist size greater than about 48 inches. In some embodiments, 7.5 times the average $t_{1/2}$ of vortioxetine can be more than about 3 to about 5 weeks in patients who have a % body fat greater than about 40%. In one embodiment, 7.5 times the average tin of vortioxetine is greater than about 3 weeks in patients who have a % body fat greater than about 40%. In some embodiments, 7.5 times the average $t_{1/2}$ of vortioxetine can be more than about 3 to about 5 weeks in patients who have a % body fat greater than about 50%. In one embodiment, 7.5 times the average $t_{1/2}$ of vortioxetine is more than about 3 weeks in patients who have a % body fat greater than about 50%.

In some embodiments, 7.5 times the average $t_{1/2}$ of vortioxetine can be greater than about 3 to about 5 weeks in patients who have android body fat greater than about 40%. In one embodiment, 7.5 times the average $t_{1/2}$ of vortioxetine is greater than about 3 weeks in patients who have android body fat greater than about 40%. In some embodiments, 7.5 times the average $t_{1/2}$ of vortioxetine can be greater than about 3 to about 5 weeks in patients who have android body fat greater than about 50%. In one embodiment, 7.5 times the average $t_{1/2}$ of vortioxetine can be greater than about 3 weeks in patients who have android body fat greater than about 50%. In some embodiments, 7.5 times the average $t_{1/2}$ of vortioxetine can be greater than about 3 to 5 weeks in patients who have gynoid body fat greater than about 40%. In one embodiment, 7.5 times the average $t_{1/2}$ of vortioxetine is greater than about 3 weeks in patients who have gynoid body fat greater than about 40%. In some embodiments, 7.5 times the average $t_{1/2}$ of vortioxetine can be greater than about 3 to about 5 weeks in patients who have gynoid body fat greater than about 50%. In some embodiments, 7.5 times the average $t_{1/2}$ of vortioxetine is greater than about 3 weeks in patients who have gynoid body fat greater than about 50%.

In some embodiments, 7.5 times the average $t_{1/2}$ of vortioxetine can be greater than about 3 to about 5 weeks in patients who have total body fat greater than about 40 kg. In one embodiment, 7.5 times the average $t_{1/2}$ of vortioxetine is greater than about 3 weeks in patients who have total body fat greater than about 40 kg. In some embodiments, 7.5 times the average $t_{1/2}$ of vortioxetine can be greater than about 4 to 6 weeks in patients who have total body fat greater than about 50 kg. In one embodiment, 7.5 times the average $t_{1/2}$ of vortioxetine is at least about 4 weeks in patients who have total body fat greater than about 50 kg. In some embodiments, 7.5 times the average $t_{1/2}$ of vortioxetine can be at least about 6 to 8 weeks (e.g. about 6, about 7, or about 8 weeks) in obese intermediate CYP2D6 metabolizers. In one embodiment, 7.5 times the average $t_{1/2}$ of vortioxetine is at least about 7 weeks in obese intermediate CYP2D6 metabolizers. In one embodiment, 7.5 times the average $t_{1/2}$ of vortioxetine is more than about 3 to about 5 weeks in non-obese intermediate CYP2D6 metabolizers. In one embodiment, 7.5 times average $t_{1/2}$ of vortioxetine is at least about 3 weeks in non-obese intermediate CYP2D6 metabolizers.

As used herein, "normal," "reference," or other derivations or variations thereof refers to a non-obese state in a person who can have at least one of the following characteristics: BMI less than about 35, % IBW less than about 150%, waist size less than about 42, % body fat less than about 40%, % android body fat less than about 40%, % gynoid body fat less than about 40%, and total body fat less than about 40 kg. Unless otherwise modified "normal metabolizer" also means an extensive CYP2D6 metabolizer.

In some embodiments, the delaying in step (b) is for at least 7.5 times the maximum $t_{1/2}$ of vortioxetine in obese patients. In some embodiments, the maximum $t_{1/2}$ of vortioxetine can be at least about 164 to 174 hours (e.g., about 164, about 165, about 166, about 167, about 168, about 169, about 170, about 171, about 172, about 173, or about 174 hours, inclusive of all ranges and subranges therebetween) in obese patients who have a BMI of at least about 35. In one embodiment, the maximum $t_{1/2}$ of vortioxetine is at least about 171 hours in obese patients who have a BMI of at least about 35. In some embodiments, the maximum $t_{1/2}$ of vortioxetine can be at least about 115 to 125 hours (e.g., about 115, about 116, about 117, about 118, about 119, 120, about 121, about 122, about 123, about 124, or about 125 hours, inclusive of all ranges and subranges therebetween) in obese patients who have a BMI of at least about 50. In one embodiment, the maximum $t_{1/2}$ of vortioxetine is at least about 129 hours in obese patients who have BMI of at least about 50. In some embodiments, the maximum $t_{1/2}$ of vortioxetine can be at least about 164 to 174 hours (e.g., about 164, about 165, about 166, about 167, about 168, about 169, about 170, about 171, about 172, about 173, or about 174 hours, inclusive of all ranges and subranges therebetween) in patients who have a BMI of at least about 40. In one embodiment, the maximum $t_{1/2}$ of vortioxetine is at least about 171 hours in patients who have a BMI of at least about 40.

In some embodiments, the maximum $t_{1/2}$ of vortioxetine can be at least about 163 to 173 hours (about 163, about 164, about 165, about 166, about 167, about 168, about 169, about 170, about 171, about 172, or about 173 hours, inclusive of all ranges and subranges therebetween) in obese patients who have a % IBW of at least about 150%. In one embodiment, the maximum $t_{1/2}$ of vortioxetine is at least about 171 hours in obese patients who have a % IBW of at least about 150%. In some embodiments, the maximum $t_{1/2}$ of vortioxetine can be at least about 115 to 125 hours (e.g., about 115, about 116, about 117, about 118, about 119, about 120, about 121, about 122, about 123, about 124, or about 125 hours, inclusive of all ranges and subranges therebetween) in obese patients who have a % IBW of at least about 250%. In one embodiment, the maximum $t_{1/2}$ of vortioxetine is at least about 129 hours in obese patients who have a % IBW of at least about 250%. In some embodiments, the maximum $t_{1/2}$ of vortioxetine can be at least about 72 to 82 hours (e.g., about 72, about 73, about 74, about 75, about 76, about 77, about 78, about 79, about 80, about 81, about 82 hours, inclusive of all ranges and subranges therebetween) in patients who have a % IBW less than about 120%. In one embodiment, the maximum $t_{1/2}$ of vortioxetine is at least about 80 hours in patients who have a % IBW less than about 120%. In some embodiments, the maximum $t_{1/2}$ of vortioxetine can be at least about 162 to 172 hours (e.g., about 162, about 163, about 164, about 165, about 166, about 167, about 168, about 169, about 170, about 171, or about 172 hours, inclusive of all ranges and subranges therebetween) in obese patients who have a waist size greater than about 42 inches. In one embodiment, the maximum $t_{1/2}$ of vortioxetine is at least about 171 hours in obese patients who have a waist size greater than about 42 inches. In some embodiments, the maximum $t_{1/2}$ of vortioxetine can be at least about 162 to 172 hours (e.g., about 162, about 163, about 164, about 165, about 166, about 167, about 168, about 169, about 170, about 171, or about 172 hours, inclusive of all ranges and subranges therebetween) in obese patients who have a waist size greater than about 48 inches. In one embodiment, the maximum $t_{1/2}$ of vortioxetine is at least about 171 hours in obese patients who have a waist size greater than about 48 inches.

In some embodiments, the maximum $t_{1/2}$ of vortioxetine can be at least about 163 to 173 hours (e.g., about 163, about 164, about 165, about 160, about 167, about 168, about 169, about 170, about 171, about 172, or about 173 hours, inclusive of all ranges and subranges therebetween) in obese patients who have a % body fat greater than about 40%. In one embodiment, the maximum $t_{1/2}$ of vortioxetine is at least about 171 hours in obese patients who have a % body fat greater than about 40%. In some embodiments, the maximum $t_{1/2}$ of vortioxetine can be at least about 115 to 130 hours (e.g., about 115, about 116, about 117, about 118, about 119, about 120, about 121, about 122, about 123, about 124, about 125, about 126, about 127, about 128 about 129 or about 130 hours, inclusive of all ranges and subranges therebetween in obese patients who have a % body fat greater than about 50%. In one embodiment, the maximum $t_{1/2}$ of vortioxetine is at least about 129 hours in obese patients who have a % body fat greater than about 50%.

In some embodiments, the maximum $t_{1/2}$ of vortioxetine can be at least about 163 to 173 hours (e.g., about 163, about 164, about 165, about 160, about 167, about 168, about 169, about 170, about 171, about 172, or about 173 hours, inclusive of all ranges and subranges therebetween) in obese patients who have android body fat greater than about 40%. In one embodiment, the maximum $t_{1/2}$ of vortioxetine is at least about 171 hours in obese patients who have android body fat greater than about 40%. In some embodiments, the maximum $t_{1/2}$ of vortioxetine can be at least about 163 to 173 hours (e.g., about 163, about 164, about 165, about 160, about 167, about 168, about 169, about 170, about 171, about 172, or about 173 hours, inclusive of all ranges and subranges therebetween) in obese patients who have android body fat greater than about 50%. In one embodiment, the maximum $t_{1/2}$ of vortioxetine is at least about 171 hours in obese patients who have android body fat greater than about 50%. In some embodiments, the maximum $t_{1/2}$ of vortioxetine can be at least about 65 to 75 hours (e.g., about 65, about 66, about 67, about 68, about 69, about 70, about 71, about 72, about 73, about 74, or about 75 hours, inclusive of all ranges and subranges therebetween) in patients who have android body fat less than about 40%. In one embodiment, the maximum $t_{1/2}$ of vortioxetine is at least about 72 hours in patients who have android body fat less than about 40%. In some embodiments, the maximum $t_{1/2}$ of vortioxetine can be at least about 115 to 130 hours (e.g., about 115, about 116, about 117, about 118, about 119, about 120, about 121, about 122, about 123, about 124, about 125, about 126, about 127, about 128, about 129, or about 130 hours, inclusive of all ranges and sub ranges therebetween) in obese patients who have gynoid body fat greater than about 40%. In one embodiment, the maximum $t_{1/2}$ of vortioxetine is at least about 129 hours in obese patients who have gynoid body fat greater than about 40%. In some embodiments, the maximum $t_{1/2}$ of vortioxetine can be at least about 115 to 130 hours (e.g., about 115, about 116, about 117, about 118, about 119, about 120, about 121, about 122, about 123, about 124, about 125, about 126, about 127, about 128, about 129 or about 130 hours, inclusive of all ranges and sub ranges therebetween) in obese patients who have gynoid body fat greater than about 50%. In one embodiment, the maximum $t_{1/2}$ of vortioxetine can be at least about 129 in obese patients who have gynoid body fat greater than about 50%.

In some embodiments, the maximum $t_{1/2}$ of vortioxetine can be at least about 163 to 173 hours (e.g., about 163, about 164, about 165, about 160, about 167, about 168, about 169, about 170, about 171, about 172, or about 173 hours, inclusive of all ranges and subranges therebetween) in patients who have total body fat greater than about 40 kg. In one embodiment, the maximum $t_{1/2}$ of vortioxetine is at least about 171 hours in patients who have total body fat greater than about 40 kg. In some embodiments, the maximum $t_{1/2}$ of vortioxetine can be at least about 163 to 173 hours (e.g., about 163, about 164, about 165, about 160, about 167, about 168, about 169, about 170, about 171, about 172, or about 173 hours, inclusive of all ranges and subranges therebetween) in patients who have total body fat greater than about 50 kg. In one embodiment, the maximum $t_{1/2}$ of vortioxetine is at least about 171 hours in patients who have total body fat greater than about 50 kg. In some embodiments, the maximum $t_{1/2}$ of vortioxetine can be at least about 72 to 82 hours (e.g., about 72, about 73, about 74, about 75, about 76, about 77, about 78, about 79, about 80, about 81, about 82 hours, inclusive of all ranges and subranges therebetween) in patients who have total body fat less than about 40 kg. In one embodiment, the maximum $t_{1/2}$ of vortioxetine is at least about 80 hours in patients who have total body fat less than about 40 kg. In some embodiments, the maximum $t_{1/2}$ of vortioxetine can be at least about 163 to 173 hours (e.g., about 163, about 164, about 165, about 166, about 167, about 168, about 169, about 170, about 171, about 72, or about 173 hours, inclusive of all ranges and subranges therebetween) in obese intermediate metabolizers. In one embodiment, the maximum $t_{1/2}$ of vortioxetine is at least about 171 hours in obese intermediate metabolizers. In some embodiments, the maximum $t_{1/2}$ of vortioxetine can be at least about 65 to 75 hours (e.g., about 65, about 66, about 67, about 68, about 69, about 70, about 71, about 72, about 73, about 74, or about 75 hours, inclusive of all ranges and subranges therebetween) in non-obese intermediate CYP2D6 metabolizers. In one embodiment, the maximum $t_{1/2}$ of vortioxetine can be at least about 72 hours in non-obese intermediate CYP2D6 metabolizers.

In some embodiments, 7.5 times the maximum $t_{1/2}$ of vortioxetine can be at least about 6, 7, or 8 weeks in patients who have BMI at least about 35. In one embodiment, 7.5 times the maximum $t_{1/2}$ of vortioxetine is at least about 7 weeks in patients who have a BMI of at least about 35. In some embodiments, 7.5 times the maximum $t_{1/2}$ of vortioxetine can be at least about 4 to 6 weeks in patients who have a BMI of at least about 50. In one embodiment, 7.5 times the maximum $t_{1/2}$ of vortioxetine is at least about 6 weeks in patients who have a BMI of at least about 50.

In some embodiments, 7.5 times the maximum $t_{1/2}$ of vortioxetine can be at least about 6 to 8 weeks in patients who have a % IBW of at least about 150%. In one embodiment, 7.5 times the maximum $t_{1/2}$ of vortioxetine can be at least about 7 weeks in obese patients who have a % IBW of at least about 150%. In some embodiments, 7.5 times the maximum $t_{1/2}$ of vortioxetine can be at least about 6 to 8 weeks in patients who have a % IBW of at least about 250%. In one embodiment, 7.5 times the maximum $t_{1/2}$ of vortioxetine is at least about 6 weeks in patients who have a % IBW of at least about 250%.

In some embodiments, 7.5 times the maximum $t_{1/2}$ of vortioxetine can be at least about 7 to 11 weeks and all ranges and subranges therebetween in patients who have a waist size greater than about 42 inches. In one embodiment, 7.5 times the maximum $t_{1/2}$ of vortioxetine is at least about 7 weeks in patients who have a waist size greater than about 42 inches. In some embodiments, 7.5 times the maximum $t_{1/2}$ of vortioxetine can be at least about 7 to 11 weeks in patients who have a waist size greater than about 48 inches. In one embodiment, 7.5 times the maximum $t_{1/2}$ of vortioxetine is at least about 7 weeks in patients who have a waist size greater than about 48 inches. In some embodiments, 7.5 times the maximum $t_{1/2}$ of vortioxetine can be at least about 7 to 11 weeks in patients who have a % body fat greater than about 40%. In one embodiment, 7.5 times the maximum $t_{1/2}$ of vortioxetine is at least about 7 weeks in patients who have a % body fat greater than about 40%. In some embodiments, 7.5 times the maximum $t_{1/2}$ of vortioxetine can be at least about 6 to 8 weeks in patients who have a % body fat greater than about 50%. In one embodiment, 7.5 times the maximum $t_{1/2}$ of vortioxetine is at least about 6 weeks in patients who have a % body fat greater than about 50%. In some embodiments, 7.5 times the maximum $t_{1/2}$ of vortioxetine can be greater than about 4 to 5 weeks in patients who have a % body fat less than about 40%. In one embodiment, 7.5 times the maximum $t_{1/2}$ of vortioxetine is at least about 4 weeks in patients who have % body fat less than about 40%.

In some embodiments, 7.5 times the maximum $t_{1/2}$ of vortioxetine can be at least about 7 to 11 weeks and all ranges and subranges therebetween in patients who have android body fat greater than about 40%. In one embodiment, 7.5 times the maximum $t_{1/2}$ of vortioxetine is at least about 7 weeks in patients who have android body fat greater than about 40%. In some embodiments, 7.5 times the maximum $t_{1/2}$ of vortioxetine can be at least about 6 to 8 weeks in patients who have android body fat greater than about 50%. In one embodiment, 7.5 times the maximum $t_{1/2}$ of vortioxetine is at least about 6 weeks in patients who have android body fat greater than about 50%.

In some embodiments, 7.5 times the maximum $t_{1/2}$ of vortioxetine can be at least about 8 to 11 weeks in patients who have gynoid body fat greater than about 40%. In one embodiment, 7.5 times the maximum $t_{1/2}$ of vortioxetine is at least about 8 weeks in patients who have gynoid body fat greater than about 40%. In some embodiments, 7.5 times the maximum $t_{1/2}$ of vortioxetine can be at least about 6 to 8 weeks in patients who have gynoid body fat greater than about 50%. In one embodiment, 7.5 times the maximum $t_{1/2}$ of vortioxetine is at least about 6 weeks in patients who have gynoid body fat greater than about 50%.

In some embodiments, 7.5 times the maximum $t_{1/2}$ of vortioxetine can be at least about 8 to 11 weeks in patients who have total body fat greater than about 40 kg. In one embodiment, 7.5 times the maximum $t_{1/2}$ of vortioxetine is at least about 8 weeks in patients who have total body fat greater than about 40 kg. In some embodiments, 7.5 times the maximum $t_{1/2}$ of vortioxetine can be at least about 8 to 11 weeks in patients who have total body fat greater than about 50 kg. In one embodiment, 7.5 times the maximum $t_{1/2}$ of vortioxetine is at least about 8 weeks in patients who have total body fat greater than about 50 kg.

In some embodiments, 7.5 times the maximum $t_{1/2}$ of vortioxetine can be at least about 8 to 9 weeks in obese intermediate CYP2D6 metabolizers. In one embodiment, 7.5 times the maximum $t_{1/2}$ of vortioxetine is at least about 8 weeks in obese intermediate CYP2D6 metabolizers. In some embodiments, 7.5 times the maximum $t_{1/2}$ of vortioxetine can be more than about 3 to 8 weeks in non-obese intermediate CYP2D6 metabolizers. In one embodiment, 7.5 times the maximum $t_{1/2}$ of vortioxetine can be about 3 weeks in non-obese intermediate CYP2D6 metabolizers.

The present disclosure also provides methods for transitioning an obese patient being treated with vortioxetine to treatment with a monoamine oxidase inhibitor (MAOI). In some embodiments, the methods comprise (a) stopping administration of vortioxetine and (b) delaying administration of the MAOI after step (a). In some embodiments, the patient described herein has at least one of the body fat characteristics as described herein. In some embodiments, the time required for delaying administration is at least the time required for the average washout plasma level of the obese patient to be equivalent to the 21 day plasma level of a normal patient.

The present disclosure also provides methods for switching patients or obese patients to a monoamine oxidase (MAOI) intended to treat psychiatric disorders. In some embodiments, the methods comprise (a) stopping administration of vortioxetine and (b) delaying administration of the MAOI after step (a). In some embodiments, the time required for delaying administration is at least the time required for the average washout plasma level of the obese patient to be equivalent to the 21 day plasma level of a normal patient. In some embodiments, the patient described herein has at least one of the obesity characteristics as described herein.

The plasma level of vortioxetine in a patient at a particular time depends upon the dose administered and the amount of time that has passed between administration of the last dose and measurement of the plasma level. Thus the plasma levels measured in a patient 21 days after ceasing administration depend on the dose of vortioxetine administered prior to ceasing administration. As used herein, therefore, "average 21 day plasma level" refers to the average vortioxetine plasma level 21 days after ceasing daily administration of a 5 mg dose of vortioxetine to a normal (non-obese patient). Because the kinetics of vortioxetine are linear, these results in terms of days to reach 21 day equivalency are extendible to other dosages such as 10 mg and 20 mg. In various embodiments, the delay time between cessation of treatment with vortioxetine and initiation of treatment with an MAOI can be determined by comparing the plasma level of an obese patient as described herein with the average 21 day plasma level of a normal patient. The delay period for an obese patient is the time required for the average plasma level of obese patients during the washout period to become equivalent to the average 21 day plasma level of a normal patient.

In some embodiments, the delaying in step (b) is for at least the time required for maximum washout plasma level (i.e. the maximum plasma level at a particular time after cessation of administration of vortioxetine) of an obese patient to be equivalent to the 21 day plasma level of a normal patient. That is, the delay in step (b) is the time required for the maximum washout plasma level in a population of obese patients (as described herein) to be equivalent to the 21 day plasma level of a normal patient. In some embodiments, the average 21 day plasma level of the normal patient is the 21 day plasma level of the average normal patient administered a daily dose of 20 mg vortioxetine and exhibiting a $t_{1/2}$ of 66 hours. In some embodiments, the average 21 day plasma level of the normal patient is the 21 day plasma level of an average normal patient administered a daily dose of 10 mg vortioxetine and exhibiting a $t_{1/2}$ of 66 hours. In other embodiments, the average 21 day plasma level of the normal patient is the 21 plasma level of an average normal patient administered a daily dose of 5 mg vortioxetine and exhibiting a $t_{1/2}$ of 66 hours.

In some embodiments, the delay or washout period in step (b) is for at least the time required for the plasma level of the patient (as described herein) to be equivalent to the 21 day plasma level of a normal patient, assuming a $t_{1/2}$ for the patient is that calculated using the formula: estimated vortioxetine $t_{1/2}=1.025$ (total body fat in kg)+17.3 (5 mg normalized steady-state vortioxetine plasma concentration in ng/mL)−55.4 (wherein the estimated $t_{1/2}$ is more than 66 hours) and the normal patient has a $t_{1/2}$ of 66 hours or 54 hours. The 21 day plasma level of the normal patient can be calculated using regression methods known in the art for a 66 hour or 54 hour $t_{1/2}$, and the delay time for the patient as described herein is calculated using the estimated vortioxetine $t_{1/2}$ equation disclosed above to calculate the time required for the patient's plasma level of vortioxetine to fall to the 21 day equivalent level of the normal patient.

In some embodiments, the obese patient can have a steady-state vortioxetine plasma level ranging from about 2 to 5 ng/ml, 5 to 13 ng/mL, for example about 2, about 3, about 4, about 5, about 6, about 7, about 8, about 9, about 10, about 11, about 12, or about 13 ng/mL, inclusive of all ranges and subranges therebetween, and any steady-state vortioxetine plasma level described herein. In one embodiment, the obese patient can have a steady-state vortioxetine plasma level of about 10 ng/mL. In one embodiment, the obese patient has a steady-state vortioxetine plasma level ranging from about 7 to 11 ng/mL.

In some embodiments, the obese patient can have a steady-state vortioxetine plasma level ranging from about 9 to 19 ng/mL, for example about 9, about 10, about 11, about 12, about 13, about 14, about 15, about 16, about 17, about 18, or about 19 ng/mL, inclusive of all ranges and subranges therebetween. In some embodiments, the obese patient has a steady-state vortioxetine plasma level ranging from about 11 to 16 ng/mL.

In some embodiments, the obese patient can have a steady-state vortioxetine plasma level greater than about 13 ng/mL, greater than about 14 ng/mL, greater than about 16 ng/mL, greater than about 17 ng/mL, greater than about 18 ng/mL, greater than about 19 ng/mL, greater than about 20 ng/mL, greater than about 21 ng/mL, greater than about 22 ng/mL, greater than about 23 ng/mL, greater than about 24 ng/mL, greater than about 25 ng/mL, greater than about 26 ng/mL, greater than about 27 ng/mL, greater than about 28 ng/mL, greater than about 29 ng/mL, greater than about 30 ng/mL, inclusive of all ranges and subranges therebetween, and any steady-state vortioxetine plasma level described herein. In one embodiment, the obese patient has a steady-state vortioxetine plasma level greater than about 16 ng/mL.

In various embodiments, any of the patients or obese patients described herein can also be an extensive CYP2D6 metabolizer, an intermediate CYP2D6 metabolizer, or a poor CYP2D6 metabolizer.

In some embodiments, the appropriate washout period for obese patients (i.e. patients having the physiological characteristics as described herein) according to the present disclosure can be calculated based on 7.5 times the estimated $t_{1/2}$ of vortioxetine in the patient, wherein $t_{1/2}$ is calculated by the following equation: estimated vortioxetine $t_{1/2}=1.025\times$(total body fat in kg)+17.3×(steady-state vortioxetine plasma concentration in ng/mL normalized to a 5 mg vortioxetine dose)−55.4, wherein said patient has an estimated half-life of greater than 66 hours.

The total body fat in kilograms can be any of the values described herein, and the 5 mg dose normalized steady-state vortioxetine plasma concentration can be any of the values described herein in any combination with the total body fat values described herein. The estimated vortioxetine $t_{1/2}$ can be at least about 67 to about 250 hours, including about 67, about 68, about 69, about 70, about 75, about 80, about 85, about 90, about 95, about 100, about 105, about 10, about 115, about 120, about 25, about 130, about 135, about 140, about 145, about 150, about 155, about 160, about 165, about 170, about 175, about 180, about 185, about 190, about 195, about 100 200, about 205, about 210, about 215, about 220, about 225, about 230, about 235, about 240, about 245, or about 250 hours, inclusive of all ranges and sub ranges therebetween.

All documents or patents cited herein are incorporated by reference in their entireties for all purposes.

The following examples are offered by way of illustration and not by way of limitation.

Example 1

To test if the obese patients would require different washout guidelines for preventing serotonin syndrome, 16 obese subjects (BMI>35) and 13 normal subjects (BMI<25) completed a clinical trial where they were administered daily with low doses (5 mg/day) of vortioxetine for 29 days in a controlled study. All subjects were subsequently tracked for 28 days after discontinuing vortioxetine on day 29. Blood samples were collected and processed according to standard techniques.

The weight, BMI, waist measurement, % body weight, % total fat, % android fat, % gynoid fat, total fat, metabolizer status, and measured half-life of each subject in shown in Table 1, below.

The plasma elimination half-life of vortioxetine was correlated to the subjects' BMI. The half-life of vortioxetine in normal subjects ranged from about 30 to 80 hours with an average of about 54 hours whereas the half-life of vortioxetine in obese subjects ranged from about 54 to 171 hours with an average of about 79 hours.

Obese subjects administered with vortioxetine 5 mg/day continued to have measurable drug plasma concentrations at least 28 days after discontinuing vortioxetine, which were as high as the highest maximum plasma concentrations of normal subjects after 2 weeks of washout. Therefore, the studies showed that obese subjects may require longer washout period after discontinuing vortioxetine and before starting monoamine oxidase inhibitors.

As shown in Table 2 and FIG. 1, the present Applicants have found that the "obese" patients exhibited a substantially higher elimination half-life compared to the "normal" patients.

TABLE 2

Half-Life in Hours

| Cohort | Min | Average | Max |
|---|---|---|---|
| Normal | 30.3 | 53.7 | 79.8 |
| Obese | 53.9 | 78.7 | 171.0 |

The 21 day "delay" period (between ceasing administration of vortioxetine and initiating administration of MAOI) provided in the TRINTELLIX label is approximately 7.5 times the elimination half-life. If the half-life values presented in Table 2 and FIG. 1 are presented as recommended delay periods, the average recommended delay for "obese"

TABLE 1

Vortioxetine Half-Life and Subject Characteristics

Figure 2:
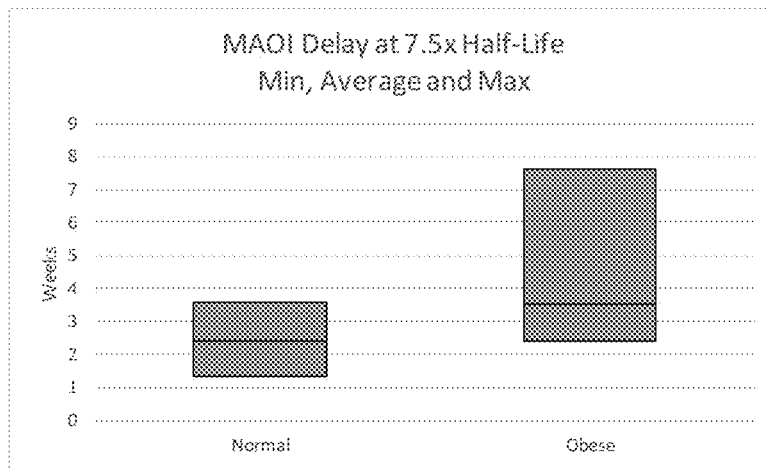
FIG. 2 is a comparison of the distribution of MAOI delay (assuming 7.5×half-life) for obese patients (BMI>35) and normal patients (BMI<25).
Figure 3:
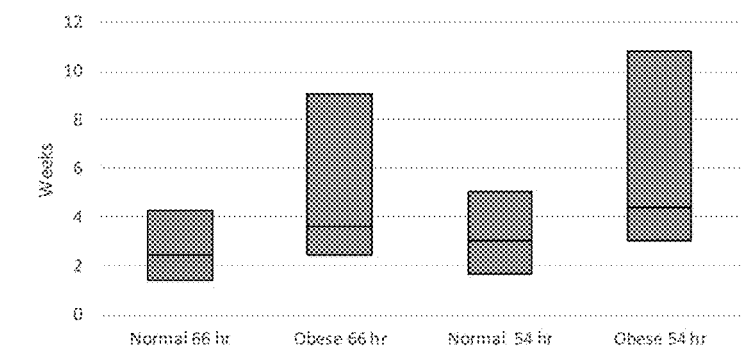
FIG. 3 is a comparison of "21 day equivalency" time for obese versus normal patients assuming 54 or 66 hour half-lives.

| Subject | $T_{1/2}$ (h) | Css (ng/mL) | Weight (kg) | BMI (kg/m²) | Waist (in) | % IBW | % Total Fat | % Android Fat | % Gynoid Fat | Total Fat (kg) | Metab. Status | Cohort |
|---|---|---|---|---|---|---|---|---|---|---|---|---|
| 01_008 | 63.9 | 5.42 | 63.0 | 22.6 | 30.7 | 107.7 | 38.2 | 38.1 | 40.5 | 24.1 | EM | Normal |
| 01_009 | 52.8 | 4.14 | 62.7 | 21.7 | 31.5 | 102.3 | 39.1 | 40.4 | 42.9 | 24.5 | EM | Normal |
| 01_010 | 50.7 | 3.13 | 62.2 | 23.6 | 31.5 | 105.4 | 28.4 | 37.4 | 34.5 | 17.7 | EM | Normal |
| 01_014 | 40.9 | 2.01 | 66.6 | 24.4 | 30.7 | 117.2 | 25.5 | 30.2 | 30.5 | 17.0 | EM | Normal |
| 01_016 | 42.1 | 3.31 | 63.9 | 24.2 | 29.9 | 117.5 | 39.4 | 45.8 | 38.3 | 25.2 | EM | Normal |
| 01_017 | 71.8 | 7.8 | 48.6 | 19.0 | 26.0 | 93.0 | 28.4 | 27.1 | 36.8 | 13.8 | IM | Normal |
| 01_019 | 48.6 | 3.29 | 75.9 | 24.0 | 33.7 | 104.4 | 29.1 | 36.7 | 30.2 | 22.1 | EM | Normal |
| 01_021 | 64.6 | 3.51 | 76.3 | 24.9 | 37.4 | 115.9 | 39.2 | 45.0 | 43.4 | 29.9 | EM | Normal |
| 01_032 | 48.3 | 4.06 | 65.3 | 24.7 | 31.5 | 119.8 | 43.0 | 45.6 | 44.6 | 28.1 | EM | Normal |
| 01_034 | 53.5 | 3.21 | 76.2 | 23.4 | 31.1 | 101.6 | 14.1 | 13.0 | 16.5 | 10.7 | EM | Normal |
| 01_037 | 30.3 | 1.4 | 82.7 | 23.4 | 32.0 | 101.1 | 24.9 | 29.7 | 26.9 | 20.6 | EM | Normal |
| 01_039 | 51.2 | 1.54 | 53.6 | 18.5 | 27.2 | 81.4 | 17.7 | 21.1 | 24.6 | 9.5 | EM | Normal |
| 01_043 | 79.8 | 5.24 | 75.4 | 23.9 | 33.1 | 110.6 | 39.4 | 44.8 | 44.0 | 29.7 | EM | Normal |
| 01_003 | 129 | 4.32 | 167.8 | 54.8 | 51.0 | 255.5 | 62.0 | 62.0 | 62.0 | 104.0 | EM | Obese |
| 01_005 | 67.8 | 4.58 | 95.4 | 41.1 | 48.0 | 209.9 | 50.6 | 51.4 | 43.9 | 48.3 | EM | Obese |
| 01_006 | 57.8 | 2.08 | 134.1 | 43.7 | 48.0 | 203.6 | 53.2 | 55.7 | 52.0 | 71.3 | EM | Obese |
| 01_013 | 93.9 | 4.57 | 101.3 | 36.1 | 42.9 | 171.5 | 52.3 | 57.3 | 53.6 | 53.0 | EM | Obese |
| 01_020 | 68.5 | 1.97 | 136.3 | 51.6 | 51.2 | 250.1 | 53.6 | 56.7 | 46.2 | 73.1 | EM | Obese |
| 01_024 | 53.9 | 3.44 | 109.0 | 35.5 | 44.1 | 165.5 | 48.2 | 51.1 | 46.8 | 52.5 | EM | Obese |
| 01_026 | 76.7 | 4.8 | 117.2 | 37.1 | 43.9 | 161.2 | 39.9 | 46.3 | 41.7 | 46.8 | EM | Obese |
| 01_033 | 74.0 | 4.75 | 107.2 | 38.6 | 44.1 | 184.0 | 51.0 | 51.0 | 51.5 | 54.7 | EM | Obese |
| 01_045 | 66.9 | 4.1 | 131.8 | 44.2 | 48.4 | 207.2 | 55.0 | 57.3 | 57.4 | 72.5 | EM | Obese |
| 01_046 | 71.0 | 3.22 | 150.4 | 57.0 | 54.0 | 276.0 | 49.3 | 53.5 | 48.1 | 74.1 | EM | Obese |
| 01_047 | 84.6 |  | 99.0 | 35.2 | 42.9 | 167.6 | 48.9 | 49.1 | 48.9 | 48.4 | EM | Obese |
| 01_048 | 56.3 | 3.39 | 109.0 | 35.5 | 42.5 | 165.5 | 45.9 | 50.4 | 42.8 | 50.0 | EM | Obese |
| 01_050 | 55.9 | 3.38 | 91.3 | 39.3 | 45.0 | 200.9 | 47.4 | 55.3 | 47.4 | 43.3 | EM | Obese |
| 01_051 | 171 | 9.27 | 135.4 | 44.1 | 48.0 | 192.3 | 41.3 | 50.5 | 38.1 | 55.9 | IM | Obese |
| 01_052 | 54.5 | 4.66 | 90.9 | 37.9 | 44.9 | 190.6 | 50.3 | 55.9 | 50.0 | 45.7 | EM | Obese |
| 01_053 | 83.7 | 4.85 | 123.1 | 36.8 | 46.5 | 159.5 | 38.4 | 50.2 | 42.0 | 47.3 | EM | Obese | patients should be longer than 21 days, and for some patients should be more than twice as long (nearly 8 weeks as shown by the "Max" values in Table 3 and FIG. 2).

TABLE 3

Delay in Weeks

MAOI Delay at 7.5 X Half-Life (Weeks)

| Cohort | Min | Average | Max |
|---|---|---|---|
| Normal | 1.4 | 2.4 | 3.6 |
| Obese | 2.4 | 3.5 | 7.6 |

Figure 4:
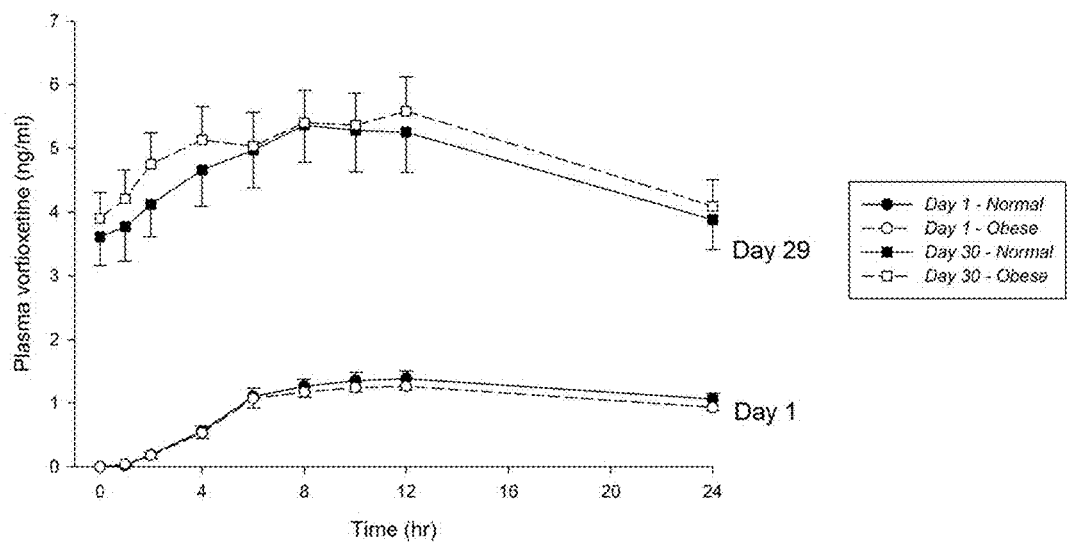
FIG. 4 shows the mean (±standard error) plasma vortioxetine concentrations during 24 hours after vortioxetine dosage in normal-weight control and obese subjects on the first and last days of administration (Day 1 and Day 30).

Another way to view the impact of obesity on vortioxetine levels during the "washout" period after ceasing vortioxetine administration is to determine the delay time required for an "obese" patient (BMI≥35) to achieve the same plasma level of vortioxetine as a "normal" patient (BMI<25) after a 21 day "washout" period. The analysis was carried out assuming normal CYP2D6 metabolizer status and either a 66 hour half-life as reported in the TRINTELLIX label, or the approximately 54 hour half-life measured in Applicants' study, above. The results are shown in FIG. 4. Similarly, the average number of weeks required for the plasma levels of obese patients to achieve "21 day equivalency" with normal patients is higher than the 3 weeks specified in the TRINTELLIX label, with most obese patients requiring a substantially longer "washout" period, as much as 3+ fold longer.

Example 2

Data obtained in the study described in Example 1 and Table 1 provided the basis for a regression model (having a $r^2$ value of 88%) based on total body fat and steady-state vortioxetine plasma concentration. Because the steady-state plasma concentration of vortioxetine correlates with metabolizer status, this regression provides a means of estimating vortioxetine half-life for patients based on total body fat and CYP2D6 metabolizer status. The results are shown in Table 4.

TABLE 4

Half-Life Estimates (hrs) Based on Total Body Fat (Kg) and Metabolizer Status

| | | Total Fat (Kg) | | | | | | | | | |
|---|---|---|---|---|---|---|---|---|---|---|---|
| | | 10 | 20 | 30 | 40 | 50 | 60 | 70 | 80 | 90 | 100 |
| Metabolizer Status | Extensive[a] | 21 | 32 | 42 | 52 | 62 | 73 | 83 | 93 | 103 | 114 |
| | Extensive[b] | 39 | 49 | 59 | 70 | 80 | 90 | 100 | 111 | 121 | 131 |
| | IM[c] | 102 | 112 | 123 | 133 | 143 | 153 | 164 | 174 | 184 | 194 |
| | IM[d] | 116 | 126 | 136 | 147 | 157 | 167 | 177 | 188 | 198 | 208 |
| | PM[e] | 215 | 225 | 235 | 245 | 256 | 266 | 276 | 286 | 297 | 307 |

[a] average of obese steady-state concentration for extensive metabolizers
[b] high of extensive metabolizers
[c] average of intermediate metabolizer (IM) values
[d] high of IM values
[e] estimated poor metabolizer (PM values).

Note that intermediate (IM) and poor metabolizer (PM) patients with very low levels of total fat (10-20 Kg) show substantially elevated half-lives compared to extensive metabolizer patients with similar levels of total body fat. This indicates that non-obese patients with intermediate or poorer CYP2D6 enzyme function require substantially longer washout periods between stopping administration of vortioxetine and initiating MAOI administration in order to reduce the risk of serotonin syndrome to risk levels found acceptable in previous studies.

The half-life values of Table 4 can alternatively be expressed as the weeks of "washout" or delay between cessation of vortioxetine administration and initiation of MAOI administration, based on 7.5×the calculated half-life (Table 5), 21 day equivalency to normal patients with a 66 hour vortioxetine half-life (Table 6), and 21 day equivalency to normal patients with a 54 hour vortioxetine half-life (Table 7). Alternatively, the delay period can be calculated based on any particular values in Table 1, or any statistical parameter for characterizing the subject population of Table, such as the arithmetic mean, geometric mean, maximum, minimum, maximum or minimum 90% confidence interval, etc. of the half-life (e.g., 7.5×the average $t_{1/2}$, 7.5×the maximum $t_{1/2}$, and so forth, or the 21 day equivalency to a normal weight extensive metabolizer subject, based on the average $t_{1/2}$ or the maximum $t_{1/2}$ or any of the aforementioned statistically parameters).

TABLE 5

Weeks of Delay (7.5 X half-life) Based on Total Body Fat (Kg) and Metabolizer Status

|  |  | Total Fat (Kg) | | | | | | | | | |
|---|---|---|---|---|---|---|---|---|---|---|---|
|  |  | 10 | 20 | 30 | 40 | 50 | 60 | 70 | 80 | 90 | 100 |
| Metabolizer Status | Extensive [a] |  |  |  |  |  | 3.2 | 3.7 | 4.2 | 4.6 | 5.1 |
|  | Extensive [b] |  |  | 3.1 | 3.6 | 4.0 | 4.5 | 4.9 | 5.4 | 5.9 |
|  | IM [c] | 4.6 | 5.0 | 5.5 | 5.9 | 6.4 | 6.8 | 7.3 | 7.8 | 8.2 | 8.7 |
|  | IM [d] | 5.2 | 5.6 | 6.1 | 6.5 | 7.0 | 7.5 | 7.9 | 8.4 | 8.8 | 9.3 |
|  | PM [e] | 9.6 | 10.0 | 10.5 | 11.0 | 11.4 | 11.9 | 12.3 | 12.8 | 13.2 | 13.7 |

[a] average of obese steady-state concentration for extensive metabolizers
[b] high of extensive metabolizers
[c] average of intermediate metabolizer (IM) values
[d] high of IM values
[e] estimated poor metabolizer (PM values).

TABLE 6

Weeks of Delay (21 day equivalency to Normal, 66 hr half-life) Based on Total Body Fat (Kg) and Metabolizer Status

|  |  | Total Fat (Kg) | | | | | | | | | |
|---|---|---|---|---|---|---|---|---|---|---|---|
|  |  | 10 | 20 | 30 | 40 | 50 | 60 | 70 | 80 | 90 | 100 |
| Metabolizer Status | Extensive [a] |  |  |  |  |  | 3.3 | 3.8 | 4.2 | 4.7 | 5.2 |
|  | Extensive [b] |  |  | 3.2 | 3.6 | 4.1 | 4.6 | 5.0 | 5.5 | 6.0 |
|  | IM [c] | 4.6 | 5.1 | 5.6 | 6.0 | 6.5 | 7.0 | 7.4 | 7.9 | 8.4 | 8.8 |
|  | IM [d] | 5.3 | 5.7 | 6.2 | 6.7 | 7.1 | 7.6 | 8.1 | 8.5 | 9.0 | 9.5 |
|  | PM [e] | 9.8 | 10.2 | 10.7 | 11.2 | 11.6 | 12.1 | 12.5 | 13.0 | 13.5 | 13.9 |

[a] average of obese steady-state concentration for extensive metabolizers
[b] high of extensive metabolizers
[c] average of intermediate metabolizer (IM) values
[d] high of IM values
[e] estimated poor metabolizer (PM values).

TABLE 7

Weeks of Delay (21 day equivalency to Normal, 54 hr half-life) Based on Total Body Fat (Kg) and Metabolizer Status

|  |  | Total Fat (Kg) | | | | | | | | | |
|---|---|---|---|---|---|---|---|---|---|---|---|
|  |  | 10 | 20 | 30 | 40 | 50 | 60 | 70 | 80 | 90 | 100 |
| Metabolizer Status | Extensive [a] |  |  |  |  | 3.5 | 4.1 | 4.6 | 5.2 | 5.8 | 6.4 |
|  | Extensive [b] |  |  | 3.3 | 3.9 | 4.5 | 5.0 | 5.6 | 6.2 | 6.7 | 7.3 |
|  | IM [c] | 5.7 | 6.3 | 6.8 | 7.4 | 8.0 | 8.6 | 9.1 | 9.7 | 10.3 | 10.8 |
|  | IM [d] | 6.5 | 7.0 | 7.6 | 8.2 | 8.8 | 9.3 | 9.9 | 10.5 | 11.0 | 11.6 |
|  | PM [e] | 12.0 | 12.6 | 13.1 | 13.7 | 14.3 | 14.8 | 15.4 | 16.0 | 16.6 | 17.1 |

[a] average of obese steady-state concentration for extensive metabolizers
[b] high of extensive metabolizers
[c] average of intermediate metabolizer (IM) values
[d] high of IM values
[e] estimated poor metabolizer (PM values).

Example 3

The clinical trials in Examples 1 and 2 are discussed in more detail below.

Overall Design

The normal-weight control group consisted of healthy male and female volunteers aged 18 to 45 years. Their body mass index (BMI) values fell in the range of 18.5 to 25 kg/m². The overweight subjects had a BMI of at least 35 kg/m². Normal weight and obese subjects were matched as closely as possible for gender and age.

Potential study participants underwent screening and evaluation within 30 days of study initiation. Procedures included: medical and psychiatric history, physical examination, electrocardiogram if indicated, hematologic and biochemical screening, and urine testing for drugs of abuse. All study participants were healthy active non-smoking adults with no history of significant medical or psychiatric disease, and taking no prescription medications. Overweight subjects were free of metabolic or other complications of obesity. Potentially child-bearing women in both groups had a negative pregnancy test, and agree to avoid the risk of pregnancy during the course of the study.

CYP2D6 genotype status was determined from whole blood samples drawn from each subject. Known alleles of CYP2D6 were tested for, as well as the presence of gene duplications (LabCorp, Inc.). CYP2D6 metabolizer status was categorized as ultra-rapid, extensive, intermediate, or poor. Ultra-rapid and poor metabolizers were not included in the study.

Subjects' waist circumference was measured manually. Percent android fat for all subjects was determined by dual energy X-ray absorptiometry (DXA).[23-26] For one subject whose weight exceeded the limits of the DXA instrumentation, percent android fat was imputed using population data available from the National Health and Nutrition Evaluation Survey (NHANES).[27,28] Total android fat (total body fat) was calculated as the product of body weight and percent android fat. Ideal body weight (IBW) was determined from actuarial data based on height and gender, and percent ideal body weight calculated as the ratio of actual weight divided by IBW.[17-19]

Statistical Power Calculation

A difference between groups in vortioxetine accumulation/elimination half-life of 40% was judged to be clinically important. Assuming a within-group standard deviation of 32% of the mean elimination half-life, the 40% between-group difference can be detected with a sample size of N=16 per group, with alpha=0.05 and at least 80% power.

Procedures

All subjects received vortioxetine, 5 mg once daily in the morning, for 29 days. The first dose was on Day 1, and the last dose was on Day 29. Blood sampling continued for another 28 days after the last dose, through Day 57.

Subjects spent 12 hours in the study unit on Day 1 (first dose of vortioxetine) and Day 29 (last dose of vortioxetine). On those two study days, venous blood samples (7 mL each) were drawn prior to the dose of vortioxetine, and at 1, 2, 4, 6, 8, 10, and 12 hours after dosage.

During the 29-day period of daily vortioxetine administration, subjects returned to the study unit in the morning of the following study days: 2, 3, 5, 8, 10, 12, 15, 17, 19, 22, 24, 26, and 29. At each visit, a single venous blood sample (7 mL) was drawn before the daily dose of vortioxetine. Subjects underwent a brief interview to assess subjective effects and possible adverse events. Subjects were then discharged until the next scheduled visit. They were provided with vortioxetine doses sufficient for daily morning administration until the next visit. No more than 2 consecutive doses of vortioxetine were taken on an outpatient basis.

On Day 29 (the final dose of vortioxetine), subjects spent 12 hours in the study unit as described above. They returned to the study unit for a single blood sample on the mornings of the following Days: 30, 31, 33, 36, 38, 40, 43, 45, 47, 50, 52, 54, and 57.

Analysis of Samples

The half-life ($T_{1/2}$) of a drug can be empirically determined by taking pharmacokinetic (PK) blood samples from a patient before, and for a period of time after, they take a drug. The length of time of PK sampling required can be estimated based on what is known from animal studies or other human studies and may range from hours to days. Ideally, an intensive blood draw schedule should be followed, with several blood draws for hours around the time of maximum drug concentration ($T_{max}$), then slowly spaced farther apart as time elapses. For example, a drug with a $T_{max}$ of 4 hours may have a sampling schedule of pre-dose, 0.5, 1, 2, 3, 4, 5, 6, 8, 10, 12, 16, and 24 hours after administration. These samples can be used to measure the plasma concentration of the drug in the patient at each time point using well-known methods such as liquid chromatography or mass spectrometry. The resulting data can be transformed by taking the natural logarithm of each number and then plotted on a graph of concentration vs. time.

Assuming first-order kinetics (the most common model for drug pharmacokinetics), once the data are plotted on a logarithmic scale, the elimination half-life can be calculated by drawing a straight line of best fit through the points in the elimination phase of the drug and finding an equation to fit that line. The slope of the line corresponds to the elimination rate constant ($K_{el}$), which can be used to calculate the half-life using the standard equation $T_{1/2}=0.693/K_{el}$. Thus, a half-life can be determined for any patient who has measurable concentrations of drug.

Plasma concentrations of vortioxetine were determined by liquid chromatography—mass spectrometry using a Shimadzu HPLC system coupled to a Sciex API-4000 mass spectrometer.

The internal standard (vortioxetine-d8) was added to calibration standards, quality control samples, and unknown study samples. All samples were extracted with methyl tert-butyl ether. The organic phase was separated and evaporated to dryness; the reconstituted extract was injected into the HPLC system. The HPLC column was a Unison UK-C18, 50 mm×2 mm, 3 micron particle size. The mobile phase consisted of an organic component (0.1% formic acid in acetonitrile) and an aqueous component (0.1% formic acid and 2 mM ammonium acetate in water). This was delivered in gradient mode at a net flow rate of 0.4 mL/min, with the organic fraction varying from 40% to 96%. m/z monitored were: 299.1/150.1 for vortioxetine, and 307.1/153 for vortioxetine-d8. The limit of quantitation was 0.1 ng/mL. The within- and between-day variability did not exceed 10%. All samples from a given study subject were extracted and analyzed at the same time using the same calibration standards.

Analysis of Data

Based on the clinical trials discussed above, several equations were derived which allow an individual to calculate the washout period (i.e., the time between stopping vortioxetine and initiating treatment with an MAOI). Data points to consisted of pre-dose plasma vortioxetine concentration (C) on each study day (t), both during (days 1-30) and after (days 30-57) the period of vortioxetine administration. The following function was fitted to data points using nonlinear regression (SAS PROC NLIN), based on methods described previously:

$$\text{For Days 1-30: } C=C_{ss}[1-\exp(-K\,t)] \quad \text{(Equation 1)}$$

$$\text{For Days 30-57: } C=C_{30}[\exp(-K(t-30))] \quad \text{(Equation 2)}$$

In this equation, $C_{ss}$ is the predicted steady-state plasma vortioxetine concentration (in ng/mL) at time "infinity," K is the rate constant (in 1/days) for drug accumulation or washout, and $C_{30}$ is the predicted concentration at t=30 Days. The half-life of accumulation or washout (in days) was calculated as: $T_{1/2}=(\ln 2)/K$. The accumulation and washout $T_{1/2}$ values were compared by linear regression analysis.

The area under the plasma vortioxetine concentration curve over a 24-hour period on Days 1 and 29 ($AUC_1$, $AUC_{29}$) was calculated using the linear trapezoidal method. The observed accumulation ratio (R) was calculated as: $R_{obs}=(AUC_{29}/AUC_1)$. The predicted accumulation ratio,[33] based on the elimination rate constant (K) and the interval between doses (1 day), was calculated as:

$$R_{pred}=1/[1-\exp(-K)] \quad \text{(Equation 3)}$$

Observed and predicted accumulation ratios were compared by linear regression.

Observed steady-state clearance of vortioxetine was calculated as: $CL_{ss,obs}=(5\text{ mg/day})/(AUC_{29})$. Linear regression was used to compare this to the predicted steady-state clearance [$CL_{ss,pred}$=(5 mg/day)/($C_{ss}$)], where $C_{ss}$ was determined as described above using Equation 1.

Differences between normal-weight and obese groups in demographic characteristics and pharmacokinetic variables were compared by Student's independent t-test. Relationships among variables were evaluated by linear or nonlinear regression analysis. Determinants of vortioxetine $T_{1/2}$ were further evaluated based on the general relation of $T_{1/2}$ to volume of distribution ($V_d$) and clearance, as follows:

$$T_{1/2} = (\text{Ln } 2) \times V_d/(\text{clearance}) \quad \text{(Equation 4)}$$

As applied to the present study, $C_{ss}$ can serve as a surrogate for clearance based on the relation between $C_{ss}$, dosing rate, and clearance. Substituting into Equation 4 yields:

$$T_{1/2} = (\text{Ln } 2) \times V_d \times C_{ss}/(5 \text{ mg/day}) \quad \text{(Equation 5)}$$

Given the constant multipliers (Ln 2, and the dosing rate of 5 mg/day), Equation 5 indicates that vortioxetine $T_{1/2}$ is proportional to the product of $V_d$ and $C_{ss}$.

Pharmacokinetics of Vortioxetine Accumulation and Washout

There was extensive accumulation of vortioxetine during the 29-day dosage period (FIG. 4), with mean observed accumulation ratios in the range of 4.5 to 5.2. The observed and predicted accumulation ratios were larger in the obese subjects than in the normal weight controls; the difference between groups was significant for the predicted ratio. Groups did not differ significantly in vortioxetine $AUC_{0-24}$ on Day 1 or Day 29, or in observed or predicted $CL_{ss}$.

Figure 5:
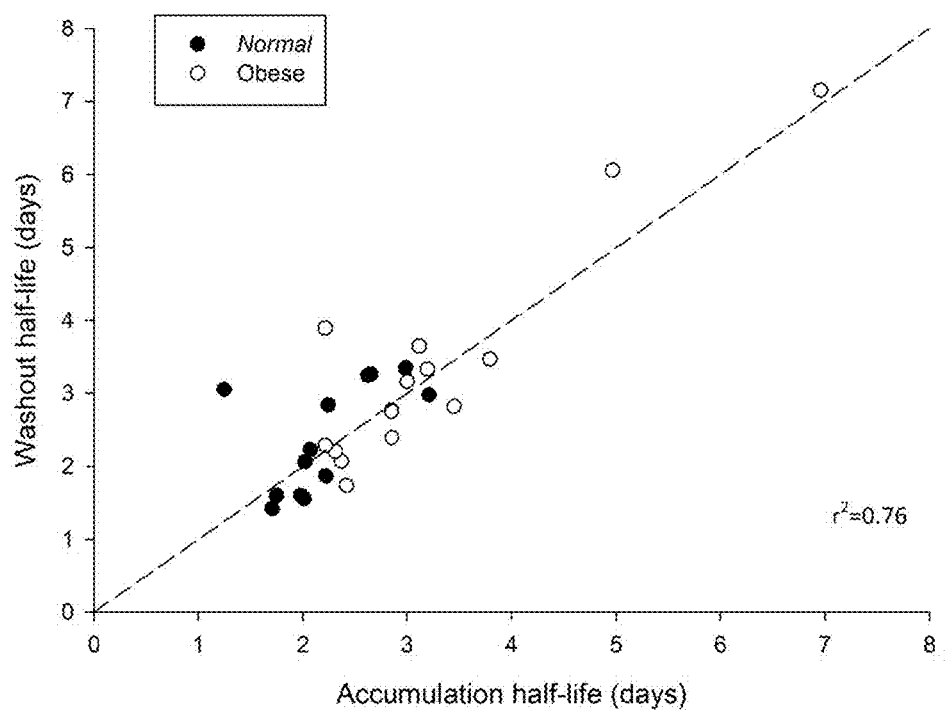
FIG. 5 shows the relation of vortioxetine accumulation half-life (X-axis) and elimination half-life (Y-axis). The dashed line is the line of identity (Y=X).
Figure 6A:
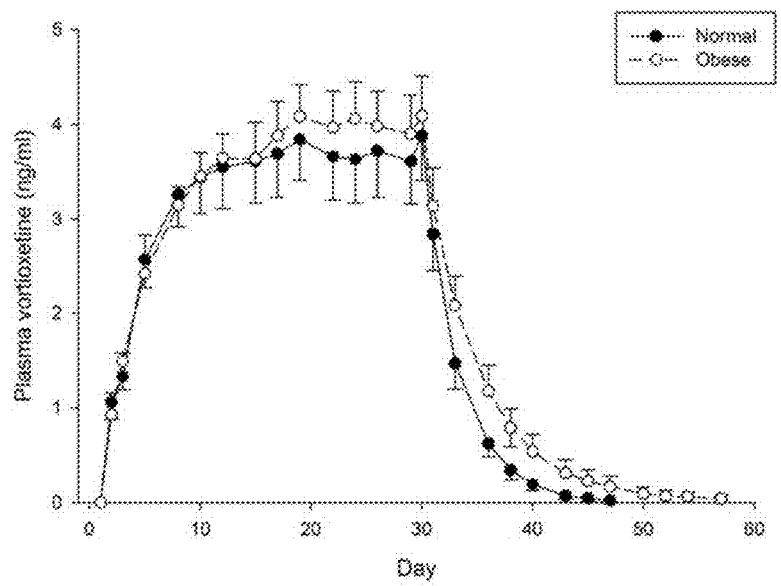
FIGS. 6A and 6B show mean (±standard error) pre-dose plasma vortioxetine concentrations during the course of the study for normal-weight control and obese subject groups.
Figure 6B:
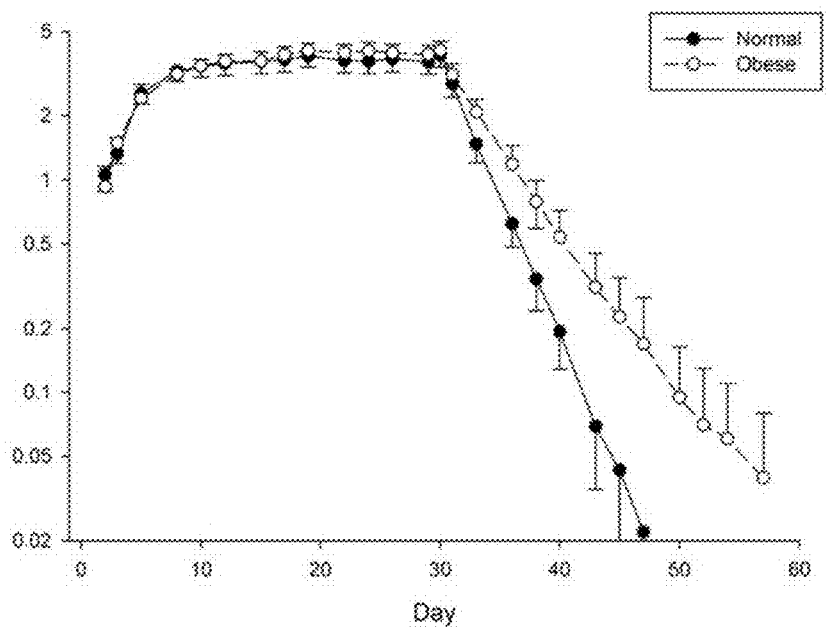

The accumulation and washout half-life values for vortioxetine were intercorrelated (FIG. 5). Both half-life values were significantly longer in obese subjects than in normal-weight controls (FIG. 6A and FIG. 6B), with mean washout half-life being 48% longer in the obese compared to the control groups (3.26 vs. 2.21 days, respectively).

Relation Between Vortioxetine Pharmacokinetics and Subject Demographics

Figure 7:
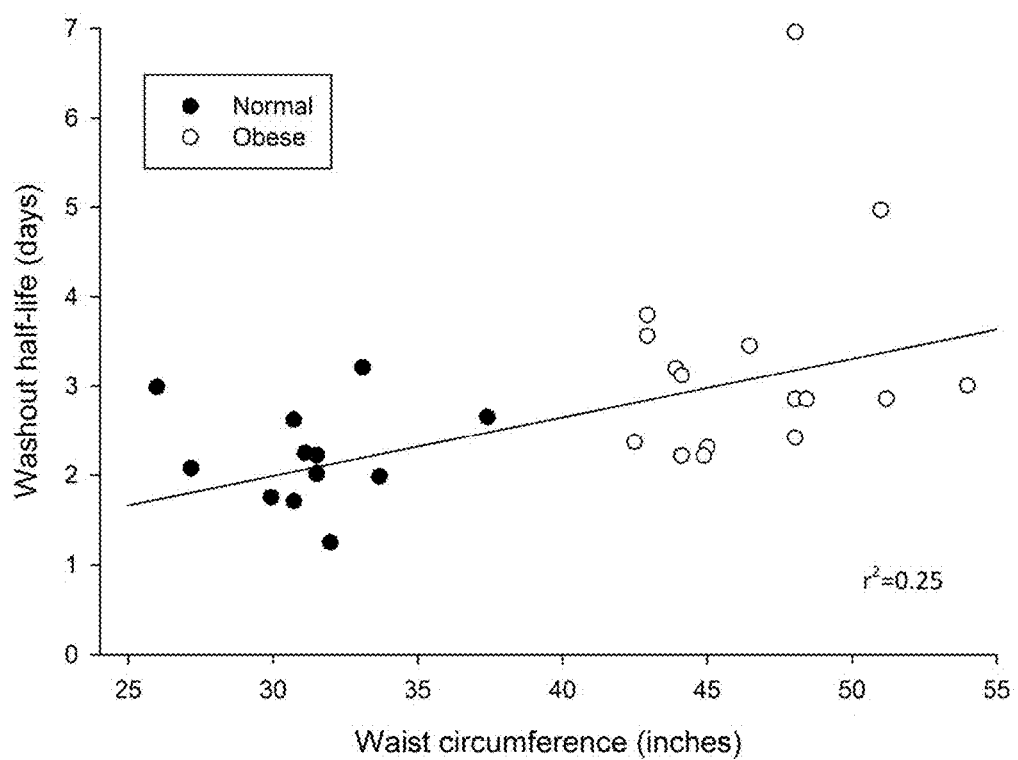
FIG. 7 shows the relation of waist circumference to vortioxetine washout half-life. The solid line represents the function determined by linear regression analysis.
Figure 8:
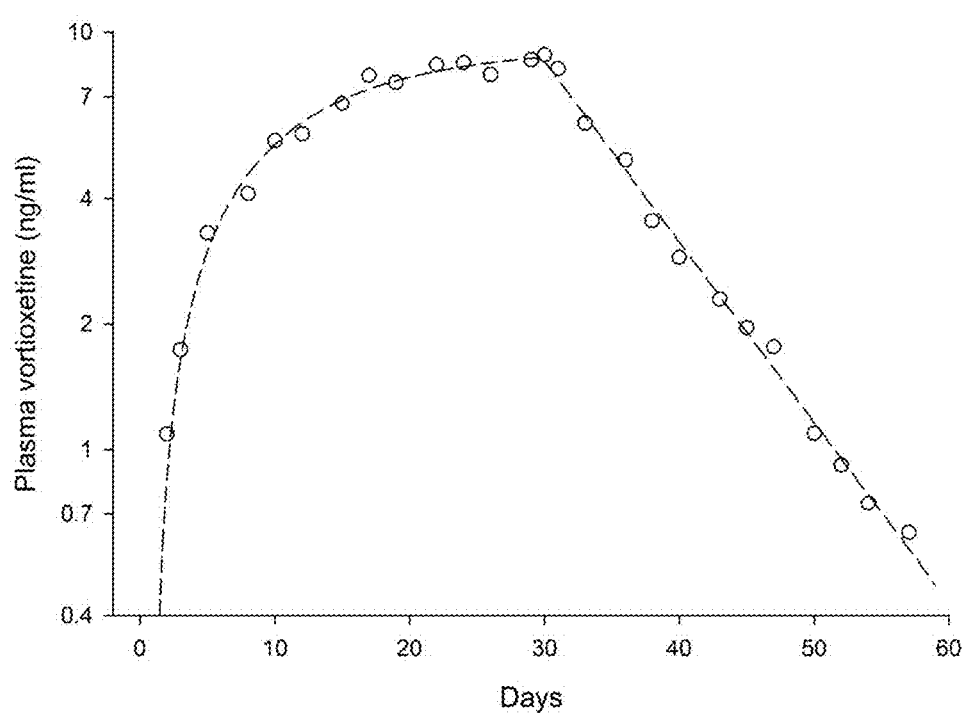
FIG. 8 shows pre-dose plasma vortioxetine concentrations in one subject from the obese group during and after the period of vortioxetine administration. Dashed lines are the functions consistent with Equation 1 (accumulation phase), and Equation 2 (post-dosage washout phase). This individual had long values of accumulation and washout half-life (7.2 and 7.0 days, respectively)

When considered outside the context of clearance or $C_{ss}$, the demographic variables representing body size or degree of obesity accounted for no more than 33% of overall variability in vortioxetine accumulation and washout half-life (FIG. 7). The incomplete associations, though statistically significant, were partly explained by very long values of accumulation half-life (7.2 days) and washout half-life (7.0 days) in one obese subject (FIG. 8). Genotype analysis of this individual indicated that he was of CYP2D6 "intermediate metabolizer" status.

A substantially greater fraction of individual variability (up to 89%) in vortioxetine half-life was explained by the product of $C_{ss}$ and measures of obesity, as predicted by Equation 5 (Table 3, FIG. 8).

Discussion

The studies described herein evaluated the accumulation and washout pharmacokinetic properties of vortioxetine in otherwise healthy obese individuals compared to healthy normal-weight controls of similar age, height, and ideal body weight. The disposition of vortioxetine in obese patients was not specifically studied as part of the drug development or approval process. However, BMI was ruled out as an important source of variance based on a population pharmacokinetic model developed by the sponsor. The present study shows that, depending on the concurrent effect of obesity on vortioxetine clearance, increased drug distribution in obese individuals could indirectly result in prolongation of accumulation and elimination half-life values.

In the present study, mean values of observed steady-state clearance were very similar between normal-weight control and obese subject groups during 29 days of once-daily administration of vortioxetine. This indicates that obesity has no apparent significant effect on vortioxetine clearance in the aggregate. Insofar as clinical efficacy and potential toxicity are related to exposure at steady-state, adjustment of customary dosage would not be needed in obese individuals on account of clearance. Further, this finding indicates that the prolongation of vortioxetine half-life in obese individuals—on average, nearly 50% longer than in normal-weight controls—is attributable to the increased extent of distribution as opposed to a change in clearance. The effect of obesity on vortioxetine half-life could have important clinical implications. The delayed attainment of steady-state after initiation of treatment may delay the onset of clinical antidepressant effect. Equally important is the delay in drug washout after termination of treatment. Current product labeling requires at least 21 days after vortioxetine discontinuation before initiation of treatment with a monoamine oxidase inhibitor (MAOI). The results of the present study indicate that this interval should be extended in obese individuals for safety reasons, due to the significantly slower post-dosage washout of vortioxetine in obese patients.

A number of indirect indices of obesity are commonly used for clinical and research purposes. These measures apply various combinations of body weight, height, age, gender, and waist circumference. A consistent finding in the literature is that these measures are intercorrelated, and it is not clearly established whether any one index is superior to another in terms of reflecting the actual degree of obesity derived from more direct measures such as percent android fat based on DXA. We observed that the relation of the indirect measures to percent android fat was not linear, probably because this percentage has an inherent "ceiling" of 65 to 70% which would be difficult to exceed even at very high body weights. However, total body fat, calculated as the product of total weight and percent android fat, was in fact linearly related to the other indirect measures. In any case, research data on body habitus for very obese individuals exceeding 175 to 200 kg in weight is sparse due to body size limitations in usual DXA instrumentation.

Despite the large and significant prolongation in vortioxetine half-life in obese individual based on aggregated data, measures of degree of obesity, whether direct or indirect, explained no more than 33% of overall variability in individual values of half-life (FIG. 7). In previous studies of other lipophilic psychotropic drugs, obesity indices explained a higher fraction of variability in half-life. In the present study, one very obese individual with a long value of half-life (FIG. 8) influenced the correlation analysis. This individual was of CYP2D6 "intermediate metabolizer" status. One normal weight control subject for which washout half-life was available group also was a CYP2D6 intermediate metabolizer. The $C_{ss}$ values for these two subjects were higher than the other study participants, reflecting lower values of clearance. With these subjects excluded from the analysis, the univariate $r^2$ value for waist circumference versus washout half-life increased to 0.37, compared to 0.25 with all subjects included (FIG. 7). In any case, the data indicates that individual variability in clearance, as reflected inversely by $C_{ss}$, also influences individual values of washout half-life (Equations 4 and 5), even though clearance did not differ between normal-weight control and obese groups in the aggregate. Up to 89% of overall variability in vortioxetine half-life was explained by the product of $C_{ss}$ and the various demographic measures of degree of obesity (FIG. 9).

Figure 9A:
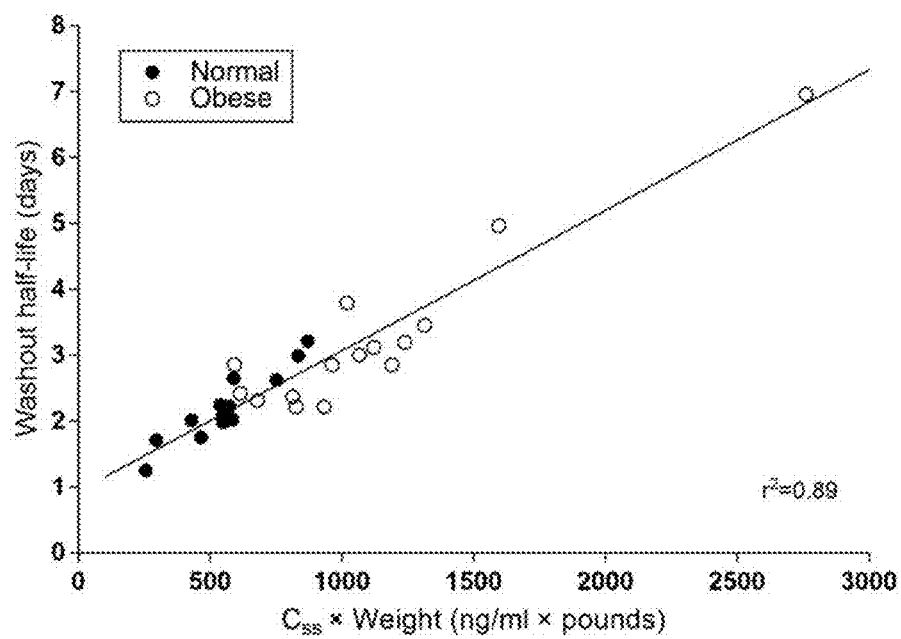
FIGS. 9A and 9B show the relation of vortioxetine washout half-life (Y-axis) to $C_{ss} \times$ body weight (left), and $C_{ss} \times$ waist circumference (right). Solid lines represent the functions determined by linear regression analysis. The regression functions are.
Figure 9B:
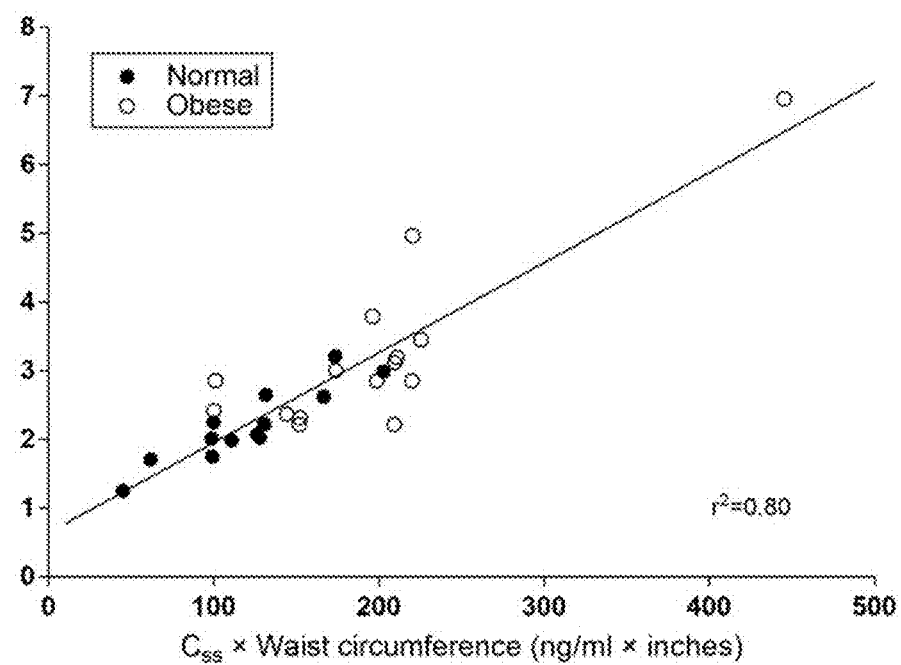

These findings in the Examples have safety implications for patients who plan to discontinue vortioxetine and initiate treatment with a monoamine oxidase inhibitor (MAOI). The current product label for vortioxetine contraindicates starting MAOI treatment until at least 21 days have elapsed after discontinuation of vortioxetine. This is due to the hazard of serotonin syndrome attributable to the pharmacodynamic interaction of the serotonergic antidepressant and the MAOI. Based on the prolongation of mean vortioxetine half-life by nearly 50% in obese patients with BMI exceeding 35 kg/m$^2$, in various embodiments, the washout period before starting MAOI treatment can be estimated as the ratio of mean obese subject half-life divided by mean control half-life, multiplied by 21 days. This calculation indicates that the washout interval between treatments should be extended to more than 21 days, e.g., at least 31 days, to assure safety in obese individuals. A second calculation approach uses Equation 2 to estimate the fraction of the steady-state concentration remaining at 21 days after discontinuation, based on the washout half-life in normal subjects. To attain a plasma concentration of vortioxetine that is about 0.14% of the initial concentration in obese individuals, in certain embodiments, a washout period of 31.5 days would be needed. In other embodiments, the washout half-life for a specific individual could be estimated using the regression relationship based on Equation 5, in which an easily-determined body size parameter (such as total weight, waist circumference, or BMI) serves as a surrogate for $V_d$ (FIGS. 9A and 9B). Using waist body weight, the washout period can be calculated as: Washout $T_{1/2}=0.00213$ ($C_{ss} \times$weight)+0.94 (see FIG. 4A); and using waist circumference, the washout period can be calculated as: Washout $T_{1/2}=0.644$ ($C_{ss} \times$waist circumference)+0.013 (see FIG. 4B).

Conclusion

This study of vortioxetine accumulation during 29 days of once-daily dosage, and of vortioxetine washout after termination of treatment, indicates that the half-life of both accumulation and washout are prolonged on average by about 50% in otherwise healthy obese individuals compared to normal-weight controls. Individual values of washout half-life are influenced by degree of obesity, as well as by vortioxetine clearance, represented inversely by $C_{ss}$, in turn potentially influenced by CYP2D6 metabolizer status. However, an individual can calculate a suitable washout period using the equations provided herein.

Embodiments

1a. A method of transitioning a patient being treated with vortioxetine to treatment with a MAOI intended to treat psychiatric disorders, comprising:
   (a) stopping administration of vortioxetine, and
   (b) administering the first dose of an MAOI more than 21 days after step (a),
   wherein said patient has at least one of the following characteristics:
      i) BMI of at least about 35;
      ii) % IBW of at least about 150%;
      iii) waist size greater than about 42 inches;
      iv) % body fat greater than about 40%;
      v) % android body fat greater than about 40%;
      vi) % gynoid body fat greater than about 40%;
      vii) total body fat greater than about 43 kg
      (viii) intermediate CYP2D6 metabolizer
      (ix) poor CYP2D6 metabolizer.

2a. The method of embodiment 1a, wherein said administering the first dose of MAOI in step (b) is at least 4 weeks after step (a).

3a. The method of embodiment 1a, wherein the patient has a BMI of at least 50.

4a. The method of embodiment 1a, wherein the patient has a % IBW of at least about 250%.

5a. The method of embodiment 1a, wherein the patient has waist size greater than about 48 inches.

6a. The method of embodiment 1a, wherein the patient has a percent body fat at least about 50%.

7a. The method of embodiment 1a, wherein the patient has a percent android body fat of at least about 50%.

8a. The method of embodiment 1a, wherein the patient has a percent gynoid body fat of at least about 50%.

9a. The method of embodiment 1a, wherein the patient has a total body fat at least about 70 kg.

10a. The method of embodiment 1a, wherein the patient is an intermediate CYP2D6 metabolizer and is not obese.

11a. The method of embodiment 1a, wherein the patient is a poor CYP2D6 metabolizer and is not obese.

12a. The method of any of embodiments 1a-9a, wherein the patient is an intermediate CYP2D6 metabolizer.

13a. The method of any of embodiments 1a-9a, wherein the patient is a poor CYP2D6 metabolizer.

1b. A method of transitioning a patient being treated with vortioxetine to treatment with a MAOI, comprising:
   (a) stopping administration of vortioxetine, and
   (b) administering the first dose of an MAOI after step (a) at a time after step (a) which is at least 7.5 times the average $t_{1/2}$ of vortioxetine in obese patients,
   wherein the patient has at least one of the following characteristics:
      i) BMI of at least about 35;
      ii) % IBW of at least about 150%;
      iii) waist size greater than about 42 inches;
      iv) % body fat greater than about 40%;
      v) % android body fat greater than about 40%;
      vi) % gynoid body fat greater than about 40%;
      vii) total body fat greater than about 40 kg
      (viii) intermediate CYP2D6 metabolizer
      (ix) poor CYP2D6 metabolizer.

2b. The method of embodiment 1b, wherein said administering the first dose of MAOI in step (b) is at least 7.5 times the maximum $t_{1/2}$ of vortioxetine in obese patients after step (a).

3b. The method of embodiment 1b, wherein said administering the first dose of MAOI in step (b) is greater than 21 days after step (a).

4b. The method of embodiment 1b, wherein said administering the first dose of MAOI in step (b) is greater than 22 days after step (a).

5b. The method of embodiment 1b, wherein the patient has a BMI of at least 50.

6b. The method of embodiment 1b, wherein the patient has a % IBW of at least about 250%.

7b. The method of embodiment 1b, wherein the patient has waist size greater than about 48 inches.

8b. The method of embodiment 1b, wherein the patient has a percent body fat at least about 50%.

9b. The method of embodiment 1b, wherein the patient has a percent android body fat of at least about 50%.

10b. The method of embodiment 1b, wherein the patient has a percent gynoid body fat of at least about 50%.

11b. The method of embodiment 1b, wherein the patient has a total body fat at least about 50 kg.

12b. The method of embodiment 1b, wherein the patient is an intermediate CYP2D6 metabolizer and is not obese.
13b. The method of embodiment 1b, wherein the patient is a poor CYP2D6 metabolizer and is not obese.
14b. The method of any of embodiments 1b-11b, wherein the patient is an intermediate CYP2D6 metabolizer.
15b. The method of any of embodiments 1b-11b, wherein the patient is a poor CYP2D6 metabolizer.
1c. A method of transitioning a patient being treated with vortioxetine to treatment with a MAOI, comprising:
 (a) stopping administration of vortioxetine, and
 (b) administering the first dose of MAOI after step (a) at a time after step (a) which is at least the time required for the average washout plasma level of obese patients to be equivalent to the average 21 day plasma level of normal patients,
 wherein the patient has at least one of the following characteristics:
  i) BMI of at least about 35;
  ii) % IBW of at least about 150%;
  iii) waist size greater than about 42 inches;
  iv) % body fat greater than about 40%;
  v) % android body fat greater than about 40%;
  vi) % gynoid body fat greater than about 40%;
  vii) total body fat greater than about 40 kg
  (viii) intermediate CYP2D6 metabolizer
  (ix) poor CYP2D6 metabolizer.
2c. The method of embodiment 1c, wherein said administering the first dose of MAOI in step (b) is at least the time after step (a) required for the maximum washout plasma level of obese patients to be equivalent to the average 21 day plasma level of normal patients.
3c. The method of embodiment 2c, wherein the average 21 day plasma level of normal patients is the average 21 day plasma level of normal patients administered a daily dose of 20 mg vortioxetine exhibiting a $t_{1/2}$ of 66 hours.
4c. The method of embodiment 2c, wherein the average 21 day plasma level of normal patients is the average 21 day plasma level of normal patients administered a daily dose of 10 mg vortioxetine exhibiting a $t_{1/2}$ of 66 hours.
5c. The method of embodiment 2c, wherein the average 21 day plasma level of normal patients is the average 21 day plasma level of normal patients administered a daily dose of 5 mg vortioxetine exhibiting a $t_{1/2}$ of 66 hours.
6c. The method of embodiment 2c, wherein the average 21 day plasma level of normal patients is the average 21 plasma level of normal patients administered a daily dose of 20 mg vortioxetine exhibiting a $t_{1/2}$ of 54 hours.
7c. The method of embodiment 2c, wherein the average 21 day plasma level of normal patients is the average 21 plasma level of normal patients administered a daily dose of 10 mg vortioxetine exhibiting a $t_{1/2}$ of 54 hours.
8c. The method of embodiment 2c, wherein the average 21 day plasma level of normal patients is the average 21 plasma level of normal patients administered a daily dose of 5 mg vortioxetine exhibiting a $t_{1/2}$ of 54 hours.
9c. The method of embodiment 1c, wherein said administering the first dose of MAOI in step (b) is more than 21 days after step (a).
10c. The method of embodiment 1c, wherein said administering the first dose of MAOI in step (b) is more than 22 days after step (a).
11c. The method of embodiment 1c, wherein the patient has a BMI of at least 50.
12c. The method of embodiment 1c, wherein the patient has a % IBW of at least about 250%.
13c. The method of embodiment 1c, wherein the patient has waist size greater than about 48 inches.
14c. The method of embodiment 1c, wherein the patient has a percent body fat at least about 50%.
15c. The method of embodiment 1c, wherein the patient has a percent android body fat of at least about 50%.
16c. The method of embodiment 1c, wherein the patient has a percent gynoid body fat of at least about 50%.
17c. The method of embodiment 1c, wherein the patient has a total body fat at least about 50 kg.
18c. The method of embodiment 1c, wherein the patient is an intermediate CYP2D6 metabolizer and is not obese.
19c. The method of embodiment 1c, wherein the patient is a poor CYP2D6 metabolizer and is not obese.
20c. The method of any of embodiments 1c-17c, wherein the patient is an intermediate CYP2D6 metabolizer.
21c. The method of any of embodiments 1c-17c, wherein the patient is a CYP2D6 poor metabolizer.
1d. A method of transitioning a patient being treated with vortioxetine to treatment with a MAOI, comprising:
 (a) stopping administration of vortioxetine, and
 (b) administering the first dose of MAOI after step (a) at a time period of at least about 7.5×estimated $t_{1/2}$ of vortioxetine, calculated by the following equation:

estimated vortioxetine $t_{1/2}$=1.025 (total body fat in kg)+17.3 (5 mg normalized steady-state vortioxetine plasma concentration in ng/mL)−55.4, wherein the estimated $t_{1/2}$ of vortioxetine is more than 66 hours.
2d. The method of embodiment 1d, wherein the patient has a 5 mg normalized steady-state vortioxetine plasma level ranging from about 2-7 ng/mL.
3d. The method of embodiment 1d, wherein the patient has a 5 mg normalized steady-state vortioxetine plasma level ranging from about 7-11 ng/mL.
4d. The method of embodiment 1d, wherein the patient has a 5 mg normalized steady-state vortioxetine plasma level ranging from about 11-16 ng/mL.
5d. The method of embodiment 1d, wherein the patient has a 5 mg normalized steady-state vortioxetine plasma level greater than about 16 ng/mL.
6d. The method of any of embodiments 1d-5d, wherein the patient is a CYP2D6 intermediate metabolizer.
7d. The method of any of embodiments 1d-5d, wherein the patient is a CYP2D6 poor metabolizer.
8d. The method of embodiment 1d, wherein the patient has a total body fat ranging from about 40-104 kg.
9d. The method of embodiment 1d, wherein when the estimated $t_{1/2}$ is more than about 110 hours, said delaying is at least 5 weeks.
10d. The method of embodiment 1d, wherein said first administering in step (b) is at least 5 weeks after step (a).
1e. A method of treating a psychiatric disorder in a patient, comprising:
 (a) administering vortioxetine; then
 (b) stopping the administration of vortioxetine; and
 (c) administering the first dose of an MAOI more than 21 days after step (b);
 wherein the psychiatric disorder is selected from the group consisting of depression, major depressive disorder, pre-menstrual dysphoric disorder, acute depressive episodes with bipolar I, treatment resistant depression, general anxiety disorder, obsessive compulsive disorder, panic disorder, post-traumatic stress disorder, social anxiety disorder, bulimia nervosa, cognitive dysfunction in pre-menstrual dysphoric disorder, attention deficit hyperactivity disorder, attention deficit hyperactivity disorder in adult patients, and combinations thereof.
2e. The method of embodiment 1e, wherein said psychiatric disorder is major depressive order.
3e. The method of embodiment 1e, wherein the MAOI is an MAOI intended to treat psychiatric disorders.
4e. The method of embodiment 1e, wherein said patient has at least one of the following characteristics:
i) BMI of at least about 35;
ii) % IBW of at least about 150%;
iii) waist size greater than about 42 inches;
iv) % body fat greater than about 40%;
v) % android body fat greater than about 40%;
vi) % gynoid body fat greater than about 40%;
vii) total body fat greater than about 40 kg
(viii) intermediate CYP2D6 metabolizer
(ix) poor CYP2D6 metabolizer.
5e. The method of embodiment, 4e, wherein the patient has a BMI of at least about 40.
6e. The method of embodiment 4e, wherein the patient has a BMI of at least 50
7e. The method of embodiment 4e, wherein the patient has a % IBW of at least about 250%.
8e. The method of embodiment 4e, wherein the patient has waist size greater than about 48 inches.
9e. The method of embodiment 4e, wherein the patient has a percent body fat of at least about 50%.
10e. The method of embodiment 4e, wherein the patient has a percent android body fat of at least about 50%.
11e. The method of embodiment 4e, wherein the patient has a percent gynoid body fat of at least about 50%.
12e. The method of embodiment 4e, wherein the patient has a total body fat of at least about 50 kg.
13e. The method of embodiment 4e, wherein the patient is an intermediate CYP2D6 metabolizer and is not obese.
14e. The method of embodiment 4e, wherein the patient is a poor CYP2D6 metabolizer and is not obese.
15e. The method of embodiment 4e, wherein the patient is an intermediate CYP2D6 metabolizer.
16e. The method of embodiment 4e, wherein the patient is an poor CYP2D6 metabolizer.
17e. The method of embodiment 4e, wherein the first dose of MAOI is administered at a time after step (b) which is at least 7.5 times the average $t_{1/2}$ of vortioxetine in obese patients.
18e. The method of embodiment 4e, wherein the first dose of MAOI is administered at a time after step (b) which is at least 7.5 times the maximum $t_{1/2}$ of vortioxetine in obese patients.
19e. The method of embodiment 4e, wherein the first dose of MAOI is administered at a time after step (b) which is at least the time required for the average washout plasma level of obese patients to be equivalent to the average 21 day plasma level of normal patients.
20e. The method of embodiment 4e, wherein the first dose of MAOI is administered at a time after step (b) which is at least about 7.5×estimated $t_{1/2}$ of vortioxetine, calculated by the following equation:

estimated vortioxetine $t_{1/2}$=1.025 (total body fat in kg)+17.3 (5 mg normalized steady-state vortioxetine plasma concentration in ng/mL)−55.4, wherein the estimated $t_{1/2}$ of vortioxetine is more than 66 hours.

21e. The method of embodiment 1e, wherein when the estimated $t_{1/2}$ is more than about 110 hours, said delaying is at least 5 weeks.
22e. The method of embodiment 1e, wherein the first dose of MAOI is administered at a time which is at least 5 weeks after step (b).
23e. The method of embodiment 1e, wherein the first dose of MAOI is administered at a time which is more than about 24 days after step (b).
24e. The method of embodiment 1e, wherein the first dose of MAOI is administered at a time after step (b) which is approximately the time required for the vortioxetine plasma level of the patient after stopping the administration of vortioxetine, to equal the plasma level of a non-obese patient administered the same dose of vortioxetine and who is an extensive CYP2D6 metabolizer with a 54 hour vortioxetine $t_{1/2}$, 21 days after the non-obese patient stops being administered the same dose of vortioxetine.
25e. The method of embodiment 1e, wherein the first dose of MAOI is administered at a time after step (b) which is approximately the time required for the vortioxetine plasma level of the patient after stopping the administration of vortioxetine, to equal the plasma level of a non-obese patient administered the same dose of vortioxetine and who is an extensive CYP2D6 metabolizer with a 66 hour vortioxetine $t_{1/2}$, 21 days after the non-obese patient stops being administered the same dose of vortioxetine.
26e. The method of embodiment 1e, wherein the first dose of MAOI is administered at a time which is at least 4 weeks after step (b).
27e. The method of embodiment 1e, wherein the first dose of MAOI is administered at a time after step (b) which is approximately the time required for the vortioxetine plasma level of the patient after stopping the administration of vortioxetine, to equal the plasma level of a normal patient administered the same dose of vortioxetine and who is an extensive CYP2D6 metabolizer with a 54 hour vortioxetine $t_{1/2}$, 21 days after the normal patient stops being administered the same dose of vortioxetine,
wherein the time after step (b) is calculated using the estimated $t_{1/2}$ for the patient using the equation:

estimated vortioxetine $t_{1/2}$=1.025 (total body fat in kg)+17.3 (5 mg normalized steady-state vortioxetine plasma concentration in ng/mL)−55.4, and wherein the estimated $t_{1/2}$ of vortioxetine is more than 66 hours.

28e. The method of embodiment 1e, wherein the first dose of MAOI is administered at a time after step (b) which is approximately the time required for the vortioxetine plasma level of the patient after stopping the administration of vortioxetine, to equal the plasma level of a normal patient administered the same dose of vortioxetine and who is an extensive CYP2D6 metabolizer with a 66 hour vortioxetine $t_{1/2}$, 21 days after the normal patient stops being administered the same dose of vortioxetine,
wherein the time after step (b) is calculated using the estimated $t_{1/2}$ for the patient using the equation:

estimated vortioxetine $t_{1/2}$=1.025 (total body fat in kg)+17.3 (5 mg normalized steady-state vortioxetine plasma concentration in ng/mL)−55.4, and wherein the estimated $t_{1/2}$ of vortioxetine is more than 66 hours.

We claim:

1. A method of treating a psychiatric disorder selected from the group consisting of depression, major depressive disorder, pre-menstrual dysphoric disorder, acute depressive episodes with bipolar I, treatment resistant depression, general anxiety disorder, obsessive compulsive disorder, panic disorder, post-traumatic stress disorder, social anxiety disorder, bulimia nervosa, cognitive dysfunction in pre-menstrual dysphoric disorder, attention deficit hyperactivity disorder, attention deficit hyperactivity disorder in adult patients, and combinations thereof in a patient, comprising:
   (a) administering vortioxetine; then
   (b) stopping the administration of vortioxetine; and
   (c) administering a first dose of an MAOI 28 or more days after step (b), wherein the patient has at least one of the following characteristics
      (i) BMI of at least about 35;
      (ii) waist size greater than about 42 inches;
      (iii) % body fat greater than about 40%;
      (iv) % android body fat greater than about 40%;
      (v) % gynoid body fat greater than about 40%; or
      (vi) total body fat greater than about 40 kg.

2. The method of claim 1, wherein the first dose of MAOI is administered at a time which is at least about 35 days after step (b).

3. The method of claim 1, wherein the first dose of MAOI is administered at a time which is in the range of from 28 days to about 42 days after step (b).

4. The method of claim 1, wherein the first dose of MAOI is administered at a time which is in the range of 28 to about 35 days after step (b).

5. The method of claim 1, wherein the first dose of MAOI is administered at a time which is about 31 days after step (b).

6. The method of claim 1, wherein the first dose of MAOI is administered at a time which is about 32 days after step (b).

7. The method of claim 1, wherein said psychiatric disorder is major depressive disorder.

8. The method of claim 1, wherein the MAOI is an MAOI intended to treat psychiatric disorders.

9. The method of claim 1, wherein said step (c) comprises administering a first dose of an MAOI 28 or more days after step (b), when the vortioxetine plasma level of the patient is no more than about 0.0057 ng/mL.

10. The method of claim 9, wherein the first dose of MAOI is administered at a time which is at least about 35 days after step (b).

11. The method of claim 9, wherein the first dose of MAOI is administered at a time which is in the range of from about 28 days to about 42 days after step (b).

12. The method of claim 9, wherein the first dose of MAOI is administered at a time which is in the range of about 28 to about 35 days after step (b).

13. The method of claim 9, wherein the first dose of MAOI is administered at a time which is about 31 days after step (b).

14. The method of claim 9, wherein the first dose of MAOI is administered at a time which is about 32 days after step (b).

15. The method of claim 9, wherein said psychiatric disorder is major depressive disorder.

16. The method of claim 9, wherein the MAOI is an MAOI intended to treat psychiatric disorders.

* * * * *